(12) United States Patent
Diaz-Chiosa

(10) Patent No.: US 11,707,276 B2
(45) Date of Patent: Jul. 25, 2023

(54) SURGICAL BUTTRESS ASSEMBLIES AND TECHNIQUES FOR SURGICAL STAPLING

(71) Applicant: Covidien LP, Mansfield, MA (US)

(72) Inventor: Olesea Diaz-Chiosa, Naugatuck, CT (US)

(73) Assignee: Covidien LP, Mansfield, MA (US)

( * ) Notice: Subject to any disclaimer, the term of this patent is extended or adjusted under 35 U.S.C. 154(b) by 44 days.

(21) Appl. No.: 17/400,153

(22) Filed: Aug. 12, 2021

(65) Prior Publication Data

US 2022/0071626 A1 Mar. 10, 2022

Related U.S. Application Data

(60) Provisional application No. 63/075,350, filed on Sep. 8, 2020.

(51) Int. Cl.
*A61B 17/072* (2006.01)
*A61B 17/068* (2006.01)
*A61B 17/00* (2006.01)

(52) U.S. Cl.
CPC ........ *A61B 17/0686* (2013.01); *A61B 17/072* (2013.01); *A61B 2017/00477* (2013.01);
(Continued)

(58) Field of Classification Search
CPC .................... A61B 17/07292; A61B 17/07207
See application file for complete search history.

(56) References Cited

U.S. PATENT DOCUMENTS 3,054,406 A 9/1962 Usher
3,124,136 A 3/1964 Usher
(Continued)

FOREIGN PATENT DOCUMENTS

CA 2282761 A1 9/1998
DE 1602563 U 3/1950
(Continued)

OTHER PUBLICATIONS

Extended European Search Report dated Jan. 4, 2022 corresponding to counterpart Patent Application EP 21195375.7.
(Continued)

*Primary Examiner* — Gloria R Weeks
(74) *Attorney, Agent, or Firm* — Carter, DeLuca & Farrell LLP

(57) ABSTRACT

A loading unit for a surgical stapling apparatus includes an anvil assembly, a staple cartridge assembly, and a surgical buttress assembly associated with the anvil or the staple cartridge assembly. Each of the anvil and staple cartridge assemblies has a tissue facing surface defining a central longitudinal slot therethrough. The surgical buttress assembly includes a buttress material positioned on the tissue facing surface of the anvil or staple cartridge assembly and a buttress frame supporting the buttress material. The buttress frame is movable from an undeployed position in which the buttress frame retains the buttress material within the boundaries of the tissue facing surface of the anvil or staple cartridge assembly to a deployed position in which the buttress frame extends the buttress material laterally outwardly from the anvil or staple cartridge assembly.

20 Claims, 9 Drawing Sheets

(52) U.S. Cl.
CPC .............. *A61B 2017/07264* (2013.01); *A61B 2017/07271* (2013.01); *A61B 2017/07278* (2013.01); *A61B 2017/07285* (2013.01)

(56) References Cited

U.S. PATENT DOCUMENTS

| | | | |
|---|---|---|---|
| 3,364,200 A | 1/1968 | Ashton et al. | |
| 3,499,591 A | 3/1970 | Green | |
| 3,797,494 A | 3/1974 | Zaffaroni | |
| 3,939,068 A | 2/1976 | Wendt et al. | |
| 3,948,666 A | 4/1976 | Kitanishi et al. | |
| 4,064,062 A | 12/1977 | Yurko | |
| 4,166,800 A | 9/1979 | Fong | |
| 4,282,236 A | 8/1981 | Broom | |
| 4,347,847 A | 9/1982 | Usher | |
| 4,354,628 A | 10/1982 | Green | |
| 4,416,698 A | 11/1983 | McCorsley, III | |
| 4,429,695 A | 2/1984 | Green | |
| 4,452,245 A | 6/1984 | Usher | |
| 4,473,077 A | 9/1984 | Noiles et al. | |
| 4,605,730 A | 8/1986 | Shalaby et al. | |
| 4,626,253 A | 12/1986 | Broadnax, Jr. | |
| 4,655,221 A | 4/1987 | Devereux | |
| 4,834,090 A | 5/1989 | Moore | |
| 4,838,884 A | 6/1989 | Dumican et al. | |
| 4,927,640 A | 5/1990 | Dahlinder et al. | |
| 4,930,674 A | 6/1990 | Barak | |
| 5,002,551 A | 3/1991 | Linsky et al. | |
| 5,014,899 A | 5/1991 | Presty et al. | |
| 5,040,715 A | 8/1991 | Green et al. | |
| 5,057,334 A | 10/1991 | Vail | |
| 5,065,929 A | 11/1991 | Schulze et al. | |
| 5,112,496 A | 5/1992 | Dhawan et al. | |
| 5,119,983 A | 6/1992 | Green et al. | |
| 5,162,430 A | 11/1992 | Rhee et al. | |
| 5,205,459 A | 4/1993 | Brinkerhoff et al. | |
| 5,263,629 A | 11/1993 | Trumbull et al. | |
| 5,281,197 A | 1/1994 | Arias et al. | |
| 5,307,976 A | 5/1994 | Olson et al. | |
| 5,312,023 A | 5/1994 | Green et al. | |
| 5,314,471 A | 5/1994 | Brauker et al. | |
| 5,318,221 A | 6/1994 | Green et al. | |
| 5,324,775 A | 6/1994 | Rhee et al. | |
| 5,326,013 A | 7/1994 | Green et al. | |
| 5,332,142 A | 7/1994 | Robinson et al. | |
| 5,344,454 A | 9/1994 | Clarke et al. | |
| 5,392,979 A | 2/1995 | Green et al. | |
| 5,397,324 A | 3/1995 | Carroll et al. | |
| 5,405,072 A | 4/1995 | Zlock et al. | |
| 5,410,016 A | 4/1995 | Hubbell et al. | |
| 5,425,745 A | 6/1995 | Green et al. | |
| 5,441,193 A | 8/1995 | Gravener | |
| 5,441,507 A | 8/1995 | Wilk | |
| 5,443,198 A | 8/1995 | Viola et al. | |
| 5,468,253 A | 11/1995 | Bezwada et al. | |
| 5,484,913 A | 1/1996 | Stilwell et al. | |
| 5,503,638 A | 4/1996 | Cooper et al. | |
| 5,514,379 A | 5/1996 | Weissleder et al. | |
| 5,542,594 A | 8/1996 | McKean et al. | |
| 5,543,441 A | 8/1996 | Rhee et al. | |
| 5,549,628 A | 8/1996 | Cooper et al. | |
| 5,550,187 A | 8/1996 | Rhee et al. | |
| 5,575,803 A | 11/1996 | Cooper et al. | |
| 5,645,915 A | 7/1997 | Kranzler et al. | |
| 5,653,756 A | 8/1997 | Clarke et al. | |
| 5,683,809 A | 11/1997 | Freeman et al. | |
| 5,690,675 A | 11/1997 | Sawyer et al. | |
| 5,702,409 A | 12/1997 | Rayburn et al. | |
| 5,752,965 A | 5/1998 | Francis et al. | |
| 5,752,974 A | 5/1998 | Rhee et al. | |
| 5,762,256 A | 6/1998 | Mastri et al. | |
| 5,766,188 A | 6/1998 | Igaki | |
| 5,769,892 A | 6/1998 | Kingwell | |
| 5,782,396 A | 7/1998 | Mastri et al. | |
| 5,799,857 A | 9/1998 | Robertson et al. | |
| 5,810,855 A | 9/1998 | Rayburn et al. | |
| 5,814,057 A | 9/1998 | Oi et al. | |
| 5,819,350 A | 10/1998 | Wang | |
| 5,833,695 A * | 11/1998 | Yoon ............... A61B 17/07207 227/176.1 |
| 5,843,096 A | 12/1998 | Igaki et al. | |
| 5,871,135 A | 2/1999 | Williamson IV et al. | |
| 5,874,500 A | 2/1999 | Rhee et al. | |
| 5,895,412 A | 4/1999 | Tucker | |
| 5,895,415 A | 4/1999 | Chow et al. | |
| 5,902,312 A * | 5/1999 | Frater ............... A61B 17/07207 606/148 |
| 5,908,427 A | 6/1999 | McKean et al. | |
| 5,915,616 A | 6/1999 | Viola et al. | |
| 5,931,847 A | 8/1999 | Bittner et al. | |
| 5,957,363 A | 9/1999 | Heck | |
| 5,964,394 A | 10/1999 | Robertson | |
| 5,964,774 A | 10/1999 | McKean et al. | |
| 5,997,895 A | 12/1999 | Narotam et al. | |
| 6,019,791 A | 2/2000 | Wood | |
| 6,030,392 A | 2/2000 | Dakov | |
| 6,032,849 A | 3/2000 | Mastri et al. | |
| 6,045,560 A | 4/2000 | McKean et al. | |
| 6,063,097 A | 5/2000 | Oi et al. | |
| 6,080,169 A | 6/2000 | Turtel | |
| 6,093,557 A | 7/2000 | Pui et al. | |
| 6,099,551 A | 8/2000 | Gabbay | |
| 6,142,933 A | 11/2000 | Longo et al. | |
| 6,149,667 A | 11/2000 | Hovland et al. | |
| 6,152,943 A | 11/2000 | Sawhney | |
| 6,155,265 A | 12/2000 | Hammerslag | |
| 6,156,677 A | 12/2000 | Brown Reed et al. | |
| 6,165,201 A | 12/2000 | Sawhney et al. | |
| 6,179,862 B1 | 1/2001 | Sawhney | |
| 6,210,439 B1 | 4/2001 | Firmin et al. | |
| 6,214,020 B1 | 4/2001 | Mulhauser et al. | |
| 6,241,139 B1 | 6/2001 | Milliman et al. | |
| 6,258,107 B1 | 7/2001 | Balazs et al. | |
| 6,267,772 B1 | 7/2001 | Mulhauser et al. | |
| 6,270,530 B1 | 8/2001 | Eldridge et al. | |
| 6,273,897 B1 | 8/2001 | Dalessandro et al. | |
| 6,280,453 B1 | 8/2001 | Kugel et al. | |
| 6,299,631 B1 | 10/2001 | Shalaby | |
| 6,309,569 B1 | 10/2001 | Farrar et al. | |
| 6,312,457 B1 | 11/2001 | DiMatteo et al. | |
| 6,312,474 B1 | 11/2001 | Francis et al. | |
| 6,325,810 B1 | 12/2001 | Hamilton et al. | |
| 6,330,965 B1 | 12/2001 | Milliman et al. | |
| 6,399,362 B1 | 6/2002 | Pui et al. | |
| 6,436,030 B2 | 8/2002 | Rehil | |
| 6,454,780 B1 | 9/2002 | Wallace | |
| 6,461,368 B2 | 10/2002 | Fogarty et al. | |
| 6,500,777 B1 | 12/2002 | Wiseman et al. | |
| 6,503,257 B2 | 1/2003 | Grant et al. | |
| 6,514,283 B2 | 2/2003 | DiMatteo et al. | |
| 6,514,534 B1 | 2/2003 | Sawhney | |
| 6,517,566 B1 | 2/2003 | Hovland et al. | |
| 6,551,356 B2 | 4/2003 | Rousseau | |
| 6,566,406 B1 | 5/2003 | Pathak et al. | |
| 6,568,398 B2 | 5/2003 | Cohen | |
| 6,590,095 B1 | 7/2003 | Schleicher et al. | |
| 6,592,597 B2 | 7/2003 | Grant et al. | |
| 6,605,294 B2 | 8/2003 | Sawhney | |
| 6,610,006 B1 | 8/2003 | Amid et al. | |
| 6,627,749 B1 | 9/2003 | Kumar | |
| 6,638,285 B2 | 10/2003 | Gabbay | |
| 6,652,594 B2 | 11/2003 | Francis et al. | |
| 6,656,193 B2 | 12/2003 | Grant et al. | |
| 6,656,200 B2 | 12/2003 | Li et al. | |
| 6,669,735 B1 | 12/2003 | Pelissier | |
| 6,673,093 B1 | 1/2004 | Sawhney | |
| 6,677,258 B2 | 1/2004 | Carroll et al. | |
| 6,685,714 B2 | 2/2004 | Rousseau | |
| 6,702,828 B2 | 3/2004 | Whayne | |
| 6,703,047 B2 | 3/2004 | Sawhney et al. | |
| 6,704,210 B1 | 3/2004 | Myers | |
| 6,723,114 B2 | 4/2004 | Shalaby | |
| 6,726,706 B2 | 4/2004 | Dominguez | |
| 6,736,823 B2 | 5/2004 | Darois et al. | |

(56) References Cited

U.S. PATENT DOCUMENTS

| | | |
|---|---|---|
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,843,252 B2 | 1/2005 | Harrison et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,214,727 B2 | 5/2007 | Kwon et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,334,717 B2 | 2/2008 | Rethy et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 * | 7/2009 | de la Torre ...... A61B 17/07207 227/176.1 |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,819,896 B2 | 10/2010 | Racenet |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 * | 5/2011 | Aranyi ............ A61B 17/07207 227/176.1 |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,256,656 B2 | 9/2012 | Milliman et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,322,590 B2 | 12/2012 | Patel et al. |
| 8,348,126 B2 | 1/2013 | Olson et al. |
| 8,348,130 B2 * | 1/2013 | Shah ................ A61B 17/07207 227/19 |
| 8,360,298 B2 | 1/2013 | Farascioni et al. |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |

(56) References Cited

U.S. PATENT DOCUMENTS

| | | | |
|---|---|---|---|
| 8,424,742 | B2 | 4/2013 | Bettuchi |
| 8,453,652 | B2 | 6/2013 | Stopek |
| 8,453,904 | B2 | 6/2013 | Eskaros et al. |
| 8,453,909 | B2 | 6/2013 | Olson et al. |
| 8,453,910 | B2 | 6/2013 | Bettuchi et al. |
| 8,464,925 | B2 | 6/2013 | Hull et al. |
| 8,470,360 | B2 | 6/2013 | McKay |
| 8,474,677 | B2 | 7/2013 | Woodard, Jr. et al. |
| 8,479,968 | B2 | 7/2013 | Hodgkinson et al. |
| 8,485,414 | B2 | 7/2013 | Criscuolo et al. |
| 8,496,683 | B2 | 7/2013 | Prommersberger et al. |
| 8,511,533 | B2 | 8/2013 | Viola et al. |
| 8,512,402 | B2 * | 8/2013 | Marczyk ............ A61B 17/068 623/2.11 |
| 8,518,440 | B2 | 8/2013 | Blaskovich et al. |
| 8,529,600 | B2 | 9/2013 | Woodard, Jr. et al. |
| 8,540,128 | B2 | 9/2013 | Shelton, IV et al. |
| 8,540,131 | B2 | 9/2013 | Swayze |
| 8,551,138 | B2 | 10/2013 | Orban, III et al. |
| 8,556,918 | B2 | 10/2013 | Bauman et al. |
| 8,561,873 | B2 | 10/2013 | Ingmanson et al. |
| 8,579,990 | B2 | 11/2013 | Priewe |
| 8,584,920 | B2 | 11/2013 | Hodgkinson |
| 8,590,762 | B2 | 11/2013 | Hess et al. |
| 8,616,430 | B2 * | 12/2013 | (Prommersberger) Stopek .......... A61B 17/0686 227/176.1 |
| 8,617,132 | B2 | 12/2013 | Golzarian et al. |
| 8,631,989 | B2 | 1/2014 | Aranyi et al. |
| 8,646,674 | B2 | 2/2014 | Schulte et al. |
| 8,668,129 | B2 | 3/2014 | Olson |
| 8,678,263 | B2 | 3/2014 | Viola |
| 8,679,137 | B2 | 3/2014 | Bauman et al. |
| 8,684,250 | B2 | 4/2014 | Bettuchi et al. |
| 8,701,958 | B2 | 4/2014 | Shelton, IV et al. |
| 8,721,703 | B2 | 5/2014 | Fowler |
| 8,727,197 | B2 | 5/2014 | Hess et al. |
| 8,757,466 | B2 | 6/2014 | Olson et al. |
| 8,789,737 | B2 | 7/2014 | Hodgkinson et al. |
| 8,814,888 | B2 | 8/2014 | Sgro |
| 8,820,606 | B2 | 9/2014 | Hodgkinson |
| 8,827,133 | B2 | 9/2014 | Shelton, IV et al. |
| 8,828,023 | B2 | 9/2014 | Neff et al. |
| 8,857,694 | B2 | 10/2014 | Shelton, IV et al. |
| 8,864,009 | B2 | 10/2014 | Shelton, IV et al. |
| 8,864,780 | B2 | 10/2014 | Euteneuer et al. |
| 8,870,050 | B2 | 10/2014 | Hodgkinson |
| 8,920,443 | B2 | 12/2014 | Hiles et al. |
| 8,920,444 | B2 | 12/2014 | Hiles et al. |
| 8,939,344 | B2 | 1/2015 | Olson et al. |
| 8,956,390 | B2 | 2/2015 | Shah et al. |
| 8,967,448 | B2 | 3/2015 | Carter et al. |
| 9,005,243 | B2 | 4/2015 | Stopek et al. |
| 9,010,606 | B2 | 4/2015 | Aranyi et al. |
| 9,010,608 | B2 | 4/2015 | Casasanta, Jr. et al. |
| 9,010,609 | B2 | 4/2015 | Carter et al. |
| 9,010,610 | B2 | 4/2015 | Hodgkinson |
| 9,010,612 | B2 | 4/2015 | Stevenson et al. |
| 9,016,543 | B2 | 4/2015 | (Prommersberger) Stopek et al. |
| 9,016,544 | B2 | 4/2015 | Hodgkinson et al. |
| 9,027,817 | B2 | 5/2015 | Milliman et al. |
| 9,044,227 | B2 | 6/2015 | Shelton, IV et al. |
| 9,055,944 | B2 | 6/2015 | Hodgkinson et al. |
| 9,084,602 | B2 | 7/2015 | Gleiman |
| 9,101,359 | B2 * | 8/2015 | Smith ............ A61B 17/07292 |
| 9,107,665 | B2 | 8/2015 | Hodgkinson et al. |
| 9,107,667 | B2 | 8/2015 | Hodgkinson |
| 9,113,871 | B2 | 8/2015 | Milliman et al. |
| 9,113,873 | B2 | 8/2015 | Marczyk et al. |
| 9,113,885 | B2 | 8/2015 | Hodgkinson et al. |
| 9,113,893 | B2 | 8/2015 | Sorrentino et al. |
| 9,161,753 | B2 | 10/2015 | Prior |
| 9,161,757 | B2 | 10/2015 | Bettuchi |
| 9,186,140 | B2 | 11/2015 | Hiles et al. |
| 9,186,144 | B2 | 11/2015 | Stevenson et al. |
| 9,192,378 | B2 | 11/2015 | Aranyi et al. |
| 9,192,379 | B2 | 11/2015 | Aranyi et al. |
| 9,192,380 | B2 | 11/2015 | (Tarinelli) Racenet et al. |
| 9,192,383 | B2 | 11/2015 | Milliman |
| 9,192,384 | B2 | 11/2015 | Bettuchi |
| 9,198,660 | B2 | 12/2015 | Hodgkinson |
| 9,198,663 | B1 | 12/2015 | Marczyk et al. |
| 9,204,881 | B2 | 12/2015 | Penna |
| 9,220,504 | B2 | 12/2015 | Viola et al. |
| 9,226,754 | B2 | 1/2016 | D'Agostino et al. |
| 9,237,892 | B2 | 1/2016 | Hodgkinson |
| 9,237,893 | B2 | 1/2016 | Carter et al. |
| 9,277,922 | B2 | 3/2016 | Carter et al. |
| 9,295,466 | B2 | 3/2016 | Hodgkinson et al. |
| 9,326,768 | B2 | 5/2016 | Shelton, IV |
| 9,326,773 | B2 | 5/2016 | Casasanta, Jr. et al. |
| 9,328,111 | B2 | 5/2016 | Zhou et al. |
| 9,345,479 | B2 | 5/2016 | (Tarinelli) Racenet et al. |
| 9,351,729 | B2 | 5/2016 | Orban, III et al. |
| 9,351,731 | B2 | 5/2016 | Carter et al. |
| 9,351,732 | B2 | 5/2016 | Hodgkinson |
| 9,358,005 | B2 | 6/2016 | Shelton, IV et al. |
| 9,364,229 | B2 | 6/2016 | D'Agostino et al. |
| 9,364,234 | B2 | 6/2016 | (Prommersberger) Stopek et al. |
| 9,386,084 | B1 * | 7/2016 | Reicher ............ G06T 11/60 |
| 9,386,988 | B2 | 7/2016 | Baxter, III et al. |
| 9,402,627 | B2 | 8/2016 | Stevenson et al. |
| 9,414,839 | B2 | 8/2016 | Penna |
| 9,433,412 | B2 | 9/2016 | Bettuchi et al. |
| 9,433,413 | B2 | 9/2016 | Stopek |
| 9,433,420 | B2 | 9/2016 | Hodgkinson |
| 9,445,812 | B2 | 9/2016 | Olson et al. |
| 9,445,817 | B2 | 9/2016 | Bettuchi |
| 9,463,260 | B2 | 10/2016 | Stopek |
| 9,486,215 | B2 | 11/2016 | Olson et al. |
| 9,492,170 | B2 | 11/2016 | Bear et al. |
| 9,504,470 | B2 | 11/2016 | Milliman |
| 9,517,164 | B2 | 12/2016 | Vitaris et al. |
| 9,522,002 | B2 * | 12/2016 | Chowaniec ......... A61B 17/072 |
| 9,572,576 | B2 | 2/2017 | Hodgkinson et al. |
| 9,585,657 | B2 | 3/2017 | Shelton, IV et al. |
| 9,597,077 | B2 | 3/2017 | Hodgkinson |
| 9,610,080 | B2 | 4/2017 | Whitfield et al. |
| 9,622,745 | B2 | 4/2017 | Ingmanson et al. |
| 9,629,626 | B2 | 4/2017 | Soltz et al. |
| 9,636,850 | B2 | 5/2017 | Stopek (nee Prommersberger) et al. |
| 9,655,620 | B2 | 5/2017 | Prescott et al. |
| 9,675,351 | B2 | 6/2017 | Hodgkinson et al. |
| 9,681,936 | B2 | 6/2017 | Hodgkinson et al. |
| 9,687,262 | B2 | 6/2017 | Rousseau et al. |
| 9,693,772 | B2 | 7/2017 | Ingmanson et al. |
| 9,708,184 | B2 | 7/2017 | Chan et al. |
| 9,770,245 | B2 | 9/2017 | Swayze et al. |
| 9,775,617 | B2 | 10/2017 | Carter et al. |
| 9,775,618 | B2 | 10/2017 | Bettuchi et al. |
| 9,782,173 | B2 | 10/2017 | Mozdzierz |
| 9,844,378 | B2 | 12/2017 | Casasanta et al. |
| 9,918,713 | B2 | 3/2018 | Zergiebel et al. |
| 9,931,116 | B2 | 4/2018 | Racenet et al. |
| 10,022,125 | B2 | 7/2018 | (Prommersberger) Stopek et al. |
| 10,098,639 | B2 | 10/2018 | Hodgkinson |
| 10,111,659 | B2 | 10/2018 | Racenet et al. |
| 10,154,840 | B2 | 12/2018 | Viola et al. |
| 10,166,023 | B2 * | 1/2019 | Vendely ............ A61B 17/07207 |
| 10,349,940 | B2 * | 7/2019 | Zeiner ............ A61B 17/068 |
| 10,729,438 | B2 * | 8/2020 | Vulhop ............ A61B 17/07292 |
| 10,952,729 | B2 * | 3/2021 | Williams ............ A61B 17/07292 |
| 10,959,731 | B2 * | 3/2021 | Casasanta, Jr. ...... A61B 17/105 |
| 11,399,833 | B2 * | 8/2022 | Abramek ............ A61B 17/07292 |
| 11,452,523 | B2 * | 9/2022 | Zeiner ............ A61B 17/068 |
| 2002/0091397 | A1 | 7/2002 | Chen |
| 2002/0151911 | A1 | 10/2002 | Gabbay |
| 2003/0065345 | A1 | 4/2003 | Weadock |
| 2003/0078209 | A1 | 4/2003 | Schmidt |
| 2003/0083676 | A1 | 5/2003 | Wallace |
| 2003/0125676 | A1 | 7/2003 | Swenson et al. |
| 2003/0181927 | A1 | 9/2003 | Wallace |
| 2003/0208231 | A1 | 11/2003 | Williamson et al. |

(56) References Cited

U.S. PATENT DOCUMENTS

| | | |
|---|---|---|
| 2004/0092912 A1 | 5/2004 | Jinno et al. |
| 2004/0093029 A1* | 5/2004 | Zubik ................. A61B 17/072 606/219 |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0006429 A1 | 1/2005 | Wales et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0149073 A1 | 7/2005 | Arani et al. |
| 2005/0283256 A1 | 12/2005 | Sommerich et al. |
| 2006/0004407 A1* | 1/2006 | Hiles ................. A61B 17/0644 606/215 |
| 2006/0008505 A1 | 1/2006 | Brandon |
| 2006/0025816 A1* | 2/2006 | Shelton ............ A61B 17/07207 606/215 |
| 2006/0121266 A1 | 6/2006 | Fandel et al. |
| 2006/0173470 A1 | 8/2006 | Oray et al. |
| 2006/0190027 A1 | 8/2006 | Downey |
| 2007/0034669 A1 | 2/2007 | de la Torre et al. |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0216855 A1 | 9/2008 | Nasca |
| 2008/0220047 A1 | 9/2008 | Sawhney et al. |
| 2008/0290134 A1 | 11/2008 | Bettuchi et al. |
| 2009/0001121 A1 | 1/2009 | Hess et al. |
| 2009/0001130 A1 | 1/2009 | Hess et al. |
| 2009/0031842 A1 | 2/2009 | Kawai et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0218384 A1 | 9/2009 | Aranyi |
| 2009/0277944 A9 | 11/2009 | Dalessandro et al. |
| 2010/0016855 A1 | 1/2010 | Ramstein et al. |
| 2010/0016888 A1 | 1/2010 | Calabrese et al. |
| 2010/0087840 A1 | 4/2010 | Ebersole et al. |
| 2010/0147921 A1 | 6/2010 | Olson |
| 2010/0147922 A1 | 6/2010 | Olson |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0331859 A1 | 12/2010 | Omori |
| 2011/0034910 A1 | 2/2011 | Ross et al. |
| 2011/0087279 A1* | 4/2011 | Shah ................. A61B 17/07207 606/219 |
| 2011/0089220 A1* | 4/2011 | Ingmanson ...... A61B 17/07207 227/176.1 |
| 2011/0125138 A1 | 5/2011 | Malinouskas et al. |
| 2011/0166673 A1 | 7/2011 | Patel et al. |
| 2011/0293690 A1 | 12/2011 | Griffin et al. |
| 2011/0315740 A1* | 12/2011 | Stopek ................. A61B 17/115 227/176.1 |
| 2012/0080336 A1 | 4/2012 | Shelton, IV et al. |
| 2012/0197272 A1 | 8/2012 | Oray et al. |
| 2012/0241491 A1 | 9/2012 | Mdridge et al. |
| 2012/0241493 A1 | 9/2012 | Baxter, III et al. |
| 2012/0253298 A1 | 10/2012 | Henderson et al. |
| 2012/0289979 A1* | 11/2012 | Eskaros ............ A61B 17/07292 606/151 |
| 2013/0153636 A1 | 6/2013 | Shelton, IV et al. |
| 2013/0153641 A1 | 6/2013 | Shelton, IV et al. |
| 2013/0221062 A1* | 8/2013 | Hodgkinson .... A61B 17/07292 227/176.1 |
| 2013/0256380 A1 | 10/2013 | Schmid et al. |
| 2013/0274722 A1* | 10/2013 | Kostrzewski .... A61B 17/00234 606/1 |
| 2014/0048580 A1 | 2/2014 | Merchant et al. |
| 2014/0061280 A1* | 3/2014 | Ingmanson ...... A61B 17/07292 227/176.1 |
| 2014/0131418 A1 | 5/2014 | Kostrzewski |
| 2014/0224686 A1 | 8/2014 | Aronhalt et al. |
| 2014/0239047 A1 | 8/2014 | Hodgkinson et al. |
| 2015/0041347 A1 | 2/2015 | Hodgkinson |
| 2015/0133995 A1 | 5/2015 | Shelton, IV et al. |
| 2015/0157320 A1 | 6/2015 | Zergiebel et al. |
| 2015/0157321 A1 | 6/2015 | Zergiebel et al. |
| 2015/0196296 A1* | 7/2015 | Swayze ............ A61B 17/07207 227/176.1 |
| 2015/0209045 A1 | 7/2015 | Hodgkinson et al. |
| 2015/0231409 A1 | 8/2015 | Racenet et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0100834 A1 | 4/2016 | Viola et al. |
| 2016/0106430 A1 | 4/2016 | Carter et al. |
| 2016/0128694 A1* | 5/2016 | Baxter, III ........... A61B 17/068 227/176.1 |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0270793 A1 | 9/2016 | Carter et al. |
| 2016/0296234 A1 | 10/2016 | Richard et al. |
| 2016/0310134 A1 | 10/2016 | Contini et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0119390 A1 | 5/2017 | Schellin et al. |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1 | 10/2017 | Ingmanson et al. |
| 2017/0354415 A1 | 12/2017 | Casasanta, Jr. et al. |
| 2017/0367694 A1* | 12/2017 | Shelton, IV ......... A61B 17/072 |
| 2018/0125491 A1 | 5/2018 | Aranyi |
| 2018/0140301 A1 | 5/2018 | Milliman |
| 2018/0168654 A1 | 6/2018 | Hodgkinson et al. |
| 2018/0214147 A1 | 8/2018 | Merchant et al. |
| 2018/0229054 A1 | 8/2018 | Racenet et al. |
| 2018/0235612 A1* | 8/2018 | Shelton, IV ...... A61B 17/07292 |
| 2018/0235617 A1* | 8/2018 | Shelton, IV ......... A61B 17/072 |
| 2018/0235621 A1* | 8/2018 | Shelton, IV ...... A61B 17/07207 |
| 2018/0235622 A1* | 8/2018 | Shelton, IV ...... A61B 17/07207 |
| 2018/0235625 A1* | 8/2018 | Shelton, IV ...... A61B 17/07292 |
| 2018/0235626 A1* | 8/2018 | Shelton, IV ...... A61B 17/07207 |
| 2018/0250000 A1 | 9/2018 | Hodgkinson et al. |
| 2018/0256164 A1 | 9/2018 | Aranyi |
| 2018/0296214 A1 | 10/2018 | Hodgkinson et al. |
| 2018/0310937 A1 | 11/2018 | (Prommersberger) Stopek et al. |
| 2018/0360460 A1 | 12/2018 | Mozdzierz et al. |
| 2019/0021734 A1 | 1/2019 | Hodgkinson |
| 2019/0046193 A1* | 2/2019 | Dunki-Jacobs ......... A61B 17/26 |
| 2019/0059878 A1 | 2/2019 | (Tarinelli) Racenet et al. |
| 2019/0083087 A1 | 3/2019 | Viola et al. |
| 2019/0254671 A1* | 8/2019 | Shankarsetty ... A61B 17/07292 |
| 2019/0343520 A1* | 11/2019 | Williams ............. A61B 17/115 |
| 2020/0107830 A1* | 4/2020 | Williams ......... A61B 17/07292 |
| 2021/0106329 A1* | 4/2021 | Williams ................ A61B 17/11 |
| 2021/0177411 A1* | 6/2021 | Williams ......... A61B 17/07207 |

(56) References Cited

U.S. PATENT DOCUMENTS

| | | | | |
|---|---|---|---|---|
| 2021/0290227 | A1* | 9/2021 | Mandula | A61B 17/0686 |
| 2022/0079581 | A1* | 3/2022 | Zeiner | A61B 17/072 |

FOREIGN PATENT DOCUMENTS

| | | | |
|---|---|---|---|
| DE | 19924311 | A1 | 11/2000 |
| EP | 0327022 | A2 | 8/1989 |
| EP | 0594148 | A1 | 4/1994 |
| EP | 2491867 | A1 | 8/2012 |
| JP | 2000166933 | A | 6/2000 |
| JP | 2002202213 | A | 7/2002 |
| JP | 2007124166 | A | 5/2007 |
| JP | 2010214132 | A | 9/2010 |
| WO | 9005489 | A1 | 5/1990 |
| WO | 95/16221 | A1 | 6/1995 |
| WO | 98/38923 | A1 | 9/1998 |
| WO | 9926826 | A2 | 6/1999 |
| WO | 0010456 | A1 | 3/2000 |
| WO | 0016684 | A1 | 3/2000 |
| WO | 2010075298 | A2 | 7/2010 |

OTHER PUBLICATIONS

Australian Examination Report No. 1 corresponding to AU 2014200793 dated Sep. 2, 2017.
Extended European Search Report corresponding to EP 17 17 8528.0 dated Oct. 13, 2017.
Australian Examination Report No. 1 corresponding to AU 2013234420 dated Oct. 24, 2017.
Japanese Office Action corresponding to JP 2013-175379 dated Oct. 20, 2017.
Japanese Office Action corresponding to JP 2013-147701 dated Oct. 27, 2017.
Extended European Search Report corresponding to EP 17 17 5656.2 dated Nov. 7, 2017.
Japanese Office Action corresponding to JP 2014-009738 dated Nov. 14, 2017.
European Office Action corresponding to EP 13 17 3986.4 dated Nov. 29, 2017.
Japanese Office Action corresponding to JP 2017-075975 dated Dec. 4, 2017.
European Office Action corresponding to EP 13 19 7958.5 dated Dec. 11, 2017.
Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.
Japanese Office Action corresponding to Patent Application JP 2013-229471 dated May 1, 2018.
Canadian Office Action corresponding to Patent Application CA 2,790,743 dated May 14, 2018.
European Office Action corresponding to Patent Application EP 14 15 7195.0 dated Jun. 12, 2018.
Extended European Search Report corresponding to Patent Application EP 12196912.5 dated Feb. 1, 2016.
Chinese Second Office Action corresponding to Patent Application CN 201610279682.3 dated Aug. 8, 2018.
Chinese Second Office Action corresponding to Patent Application CN 201410588811.8 dated Aug. 27, 2018.
Extended European Search Report corresponding to Patent Application EP 18160809.2 dated Sep. 18, 2018.
Extended European Search Report corresponding to Patent Application EP 18192317.8 dated Dec. 20, 2018.
Extended European Search Report corresponding to Patent Application EP 18190154.7 dated Feb. 4, 2019.
European Office Action corresponding to EP 14 17 2681.0 dated May 13, 2016.
Extended European Search Report corresponding to EP 16 15 3647.9 dated Jun. 3, 2016.
Chinese Office Action corresponding to CN 201210545228 dated Jun. 29, 2016.
Japanese Office Action corresponding to JP 2012-250058 dated Jun. 29, 2016.
European Office Action corresponding to EP 14 15 7997.9 dated Jun. 29, 2016.
Canadian Office Action corresponding to CA 2,712,617 dated Jun. 30, 2016.
Chinese First Office Action corresponding to CN 2013103036903 dated Jun. 30, 2016.
Australian Patent Examination Report No. 1 corresponding to AU 2012250278 dated Jul. 10, 2016.
Australian Patent Examination Report No. 1 corresponding to AU 2012244382 dated Jul. 10, 2016.
Japanese Office Action corresponding to 2012-255242 dated Jul. 26, 2016.
Japanese Office Action corresponding to JP 2012-268668 dated Jul. 27, 2016.
European Office Action corresponding to EP 14 15 2060.1 dated Aug. 4, 2016.
European Office Action corresponding to EP 12 16 5609.4 dated Aug. 5, 2016.
European Office Action corresponding to EP 15 15 2392.5 dated Aug. 8, 2016.
Japanese Office Action corresponding to JP 2013-003624 dated Aug. 25, 2016.
Australian Patent Examination Report No. 1 corresponding to AU 2012261752 dated Sep. 6, 2016.
Japanese Office Action corresponding to JP 2014-252703 dated Sep. 26, 2016.
European Office Action corresponding to EP 12 19 8776.2 dated Sep. 12, 2016.
Japanese Office Action corresponding to JP 2013-000321 dated Sep. 13, 2016.
Chinese Second Office Action corresponding to CN 201310353628.5 dated Sep. 26, 2016.
European Office Action corresponding to EP 12 15 2541.4 dated Sep. 27, 2016.
Australian Patent Examination Report No. 1 corresponding to AU 2012268923 dated Sep. 28, 2016.
Chinese First Office Action corresponding to CN 2013107068710 dated Dec. 16, 2016.
Chinese First Office Action corresponding to CN 201310646606.8 dated Dec. 23, 2016.
Japanese Office Action corresponding to JP 2013-000321 dated Jan. 4, 2017.
Extended European Search Report corresponding to EP 16 16 6367.9 dated Jan. 16, 2017.
Australian Examination Report No. 1 corresponding to AU 2013206777 dated Feb. 1, 2017.
Chinese Second Office Action corresponding to CN 2013103036903 dated Feb. 23, 2017.
Japanese Office Action corresponding to JP 2013-175379 dated Mar. 1, 2017.
Chinese First Office Action corresponding to CN 201410028462.4 dated Mar. 2, 2017.
Chinese First Office Action corresponding to CN 201410084070 dated Mar. 13, 2017.
Extended European Search Report corresponding to EP 16 19 6549.6 dated Mar. 17, 2017.
Japanese Office Action corresponding to JP 2013-147701 dated Mar. 21, 2017.
Australian Examination Report No. 1 corresponding to AU 2013206804 dated Mar. 21, 2017.
Australian Examination Report No. 1 corresponding to AU 2013211499 dated May 4, 2017.

(56) References Cited

OTHER PUBLICATIONS

Australian Examination Report No. 1 corresponding to AU 2014201008 dated May 23, 2017.
European Office Action corresponding to EP 15 17 4146.9 dated May 15, 2017.
Japanese Office Action corresponding to JP 2013-154561 dated May 23, 2017.
European Office Action corresponding to EP 12 19 4784.0 dated May 29, 2017.
Japanese Office Action corresponding to JP 2013-169083 dated May 31, 2017.
Australian Examination Report No. 1 corresponding to AU 2013213767 dated Jun. 29, 2017.
Australian Examination Report No. 2 corresponding to AU 2012261752 dated Jul. 7, 2017.
Australian Examination Report No. 1 corresponding to AU 2013266989 dated Jul. 10, 2017.
Extended European Search Report corresponding to EP 14 15 3609.4 dated Jul. 14, 2017.
Australian Examination Report No. 1 corresponding to AU 2013234418 dated Jul. 14, 2017.
Extended European Search Report corresponding to EP 14 15 3610.2 dated Jul. 17, 2017.
Australian Examination Report No. 1 corresponding to AU 2014200109 dated Jul. 20, 2017.
Australian Examination Report No. 1 corresponding to AU 2014200074 dated Jul. 20, 2017.
Japanese Office Action corresponding to JP 2013-250857 dated Aug. 17, 2017.
Japanese Office Action corresponding to JP 2013-229471 dated Aug. 17, 2017.
European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).
Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).
Extended European Search Report corresponding to EP 14 16 9739.1, completed Aug. 19, 2014 and dated Aug. 29, 2014; (7 pp).
Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).

(56) References Cited

OTHER PUBLICATIONS

Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).
Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
European Office Action corresponding to EP 12 198 776.2 dated Apr. 7, 2015.
European Office Action corresponding to EP 13 156 297.7 dated Apr. 10, 2015.
Australian Examination Report No. 1 corresponding to AU 2011250822 dated May 18, 2015.
European Office Action corresponding to EP 12 186 175.1 dated Jun. 1, 2015.
Chinese Office Action corresponding to CN 201010517292.8 dated Jun. 2, 2015.
Extended European Search Report corresponding to EP 14 17 4814.5 dated Jun. 9, 2015.
Australian Examination Report No. 1 corresponding to AU 2014200584 dated Jun. 15, 2015.
European Office Action corresponding to EP 13 180 881.8 dated Jun. 19, 2015.
European Office Action corresponding to EP 14 157 195.0 dated Jul. 2, 2015.
Extended European Search Report corresponding to EP 12 19 6902.6 dated Aug. 6, 2015.
Extended European Search Report corresponding to EP 14 15 2060.1 dated Aug. 14, 2015.
Chinese Office Action corresponding to CN 201210129787.2 dated Aug. 24, 2015.
Canadian Office Action corresponding to CA 2,665,206 dated Nov. 19, 2013.
Chinese Notification of Reexamination corresponding to CN 201010517292.8 dated Jun. 2, 2015.
Japanese Office Action corresponding to JP 2014-216989 dated Sep. 11, 2015.
Canadian First Office Action corresponding to CA 2,686,105 dated Sep. 17, 2015.
Japanese Office Action corresponding to JP 2012-040188 dated Oct. 21, 2015.
European Communication corresponding to EP 13 17 6895.4 dated Nov. 5, 2015.
Chinese First Office Action corresponding to CN 201210544552 dated Nov. 23, 2015.
Chinese First Office Action corresponding to CN 201210545228 dated Nov. 30, 2015.
Extended European Search Report corresponding to EP 15 18 0491.1 dated Dec. 9, 2015.
Extended European Search Report corresponding to EP 15 18 3819.0 dated Dec. 11, 2015.
Canadian Office Action corresponding to CA 2,697,819 dated Jan. 6, 2016.
Canadian Office Action corresponding to CA 2,696,419 dated Jan. 14, 2016.
European Office Action corresponding to EP 12 19 8776.2 dated Jan. 19, 2016.
Extended European Search Report corresponding to EP 15 17 4146.9 dated Jan. 20, 2016.
Chinese First Office Action corresponding to CN 201310353628.5 dated Jan. 25, 2016.
Extended European Search Report corresponding to EP 12 19 6912.5 dated Feb. 1, 2016.
Japanese Office Action corresponding to JP 2012-098903 dated Feb. 22, 2016.
Extended European Search Report corresponding to EP 12 19 8753.1 dated Feb. 24, 2016.
Chinese First Office Action corresponding to CN 201410449019.4 dated Mar. 30, 2016.
Extended European Search Report corresponding to EP 16 15 0232.3 dated Apr. 12, 2016.
European Office Action corresponding to EP 11 18 3256.4 dated Apr. 20, 2016.
Australian Examination Report No. 1 corresponding to AU 2012244169 dated May 10, 2016.
European Office Action corresponding to EP 10 25 0715.9 dated May 12, 2016.
Chinese First Office Action corresponding to CN 201410778512.0 dated May 13, 2016.
Australian Examination Report No. 1 corresponding to AU 2012227358 dated May 16, 2016.
Japanese Office Action corresponding to JP 2012-040188 dated May 17, 2016.
Australian Examination Report No. 1 corresponding to AU 2012244380 dated May 20, 2016.
Australian Examination Report No. 1 corresponding to AU 2014227480 dated May 21, 2016.
Australian Examination Report No. 1 corresponding to AU 2012254977 dated May 30, 2016.

* cited by examiner

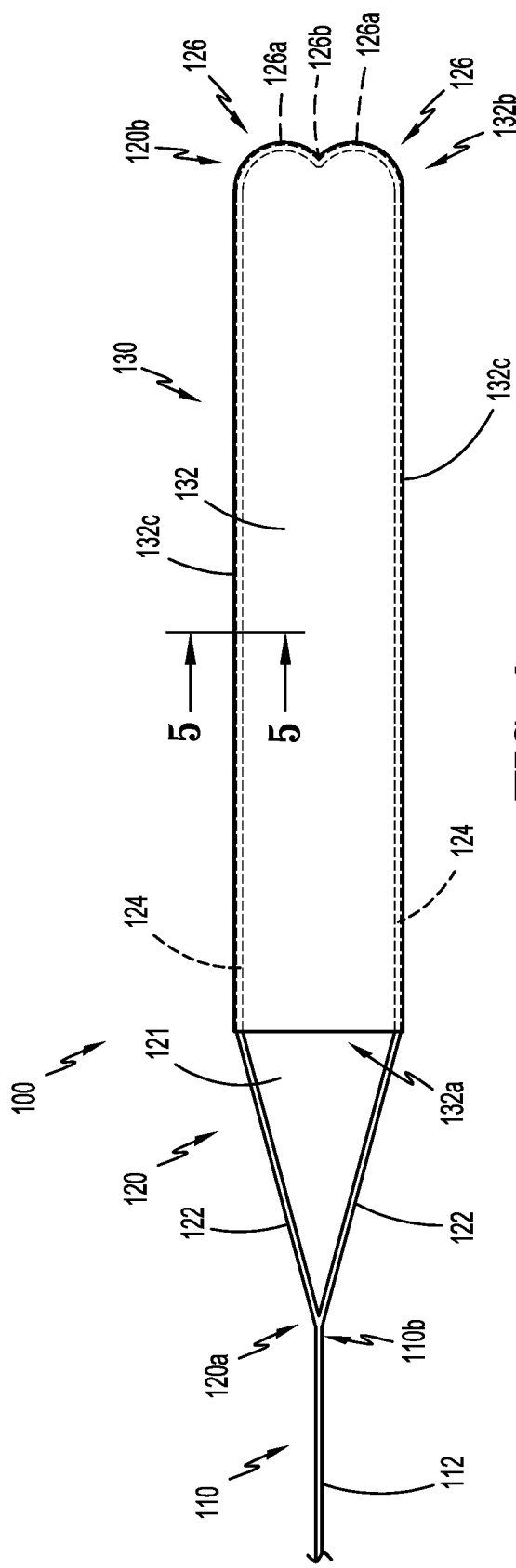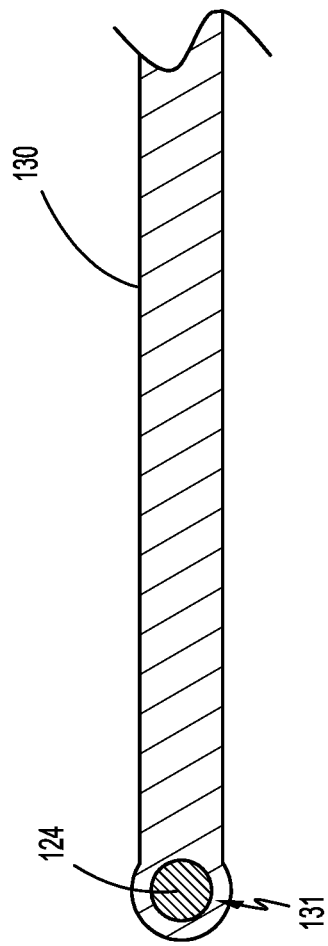

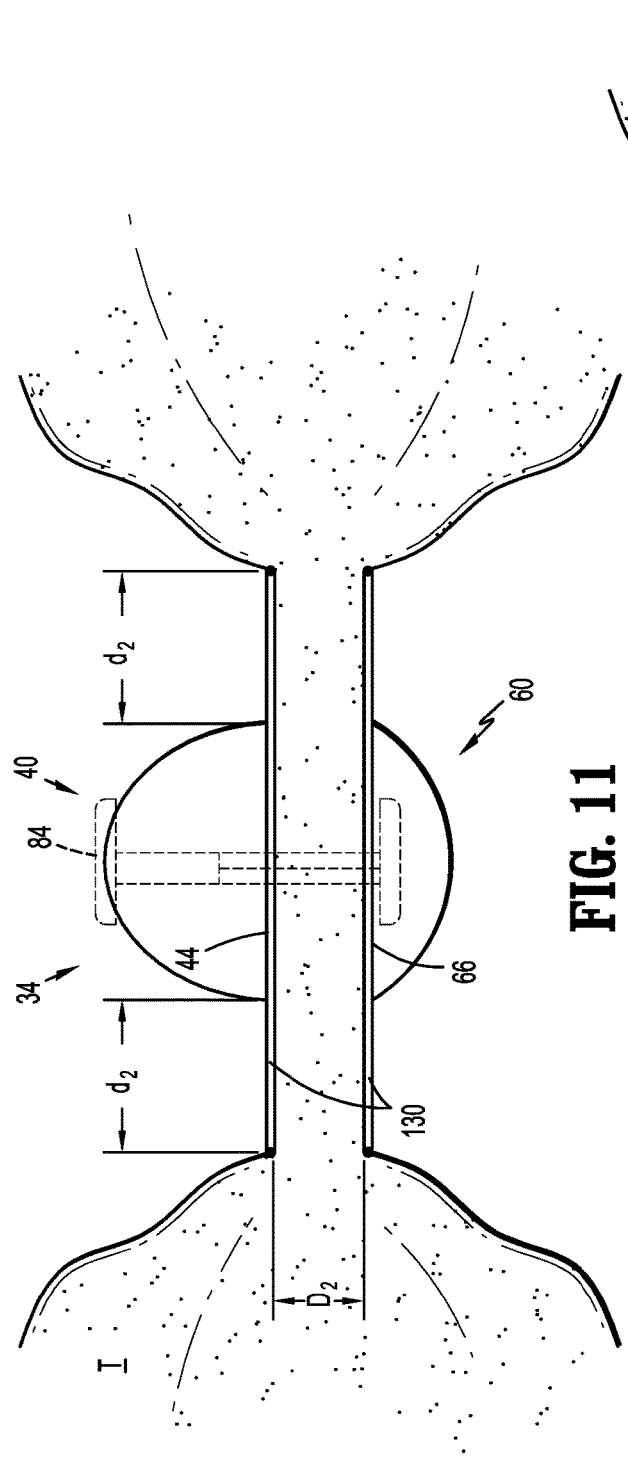
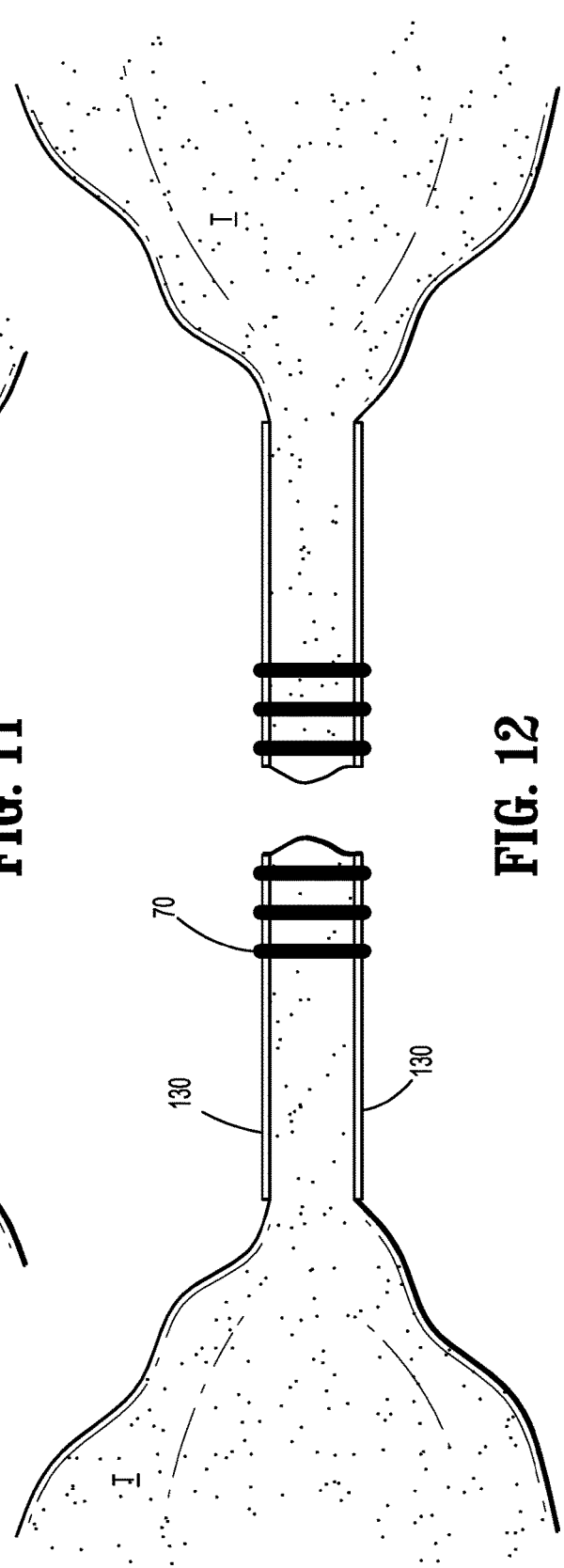

SURGICAL BUTTRESS ASSEMBLIES AND TECHNIQUES FOR SURGICAL STAPLING

CROSS-REFERENCE TO RELATED APPLICATION

The present application claims the benefit of and priority to U.S. Provisional Patent Application Ser. No. 63/075,350, filed on Sep. 8, 2020, the entire content of which being hereby incorporated by reference.

FIELD

The present application is generally related to surgical stapling apparatus, and more particularly, to surgical buttress assemblies for surgical stapling apparatus and techniques for surgical stapling utilizing the surgical buttress assemblies.

BACKGROUND

Surgical stapling apparatus are employed by surgeons to sequentially or simultaneously apply one or more rows of fasteners, e.g., staples or two-part fasteners, to body tissue for the purpose of joining segments of body tissue together. Such apparatus generally include a pair of jaws or finger-like structures between which the body tissue to be joined is placed. When the surgical stapling apparatus is actuated, or "fired", longitudinally moving firing bars contact staple drive members in one of the jaws. The staple drive members push the surgical staples through the body tissue and into an anvil in the opposite jaw which forms the staples. If body tissue is to be removed or separated, a knife blade can be provided in the jaws of the apparatus to cut the body tissue between the lines of staples.

Surgical supports, e.g., meshes or buttress materials, may be used in combination with surgical stapling apparatus to bridge, repair, and/or reinforce tissue defects within a patient. The buttress material reinforces the staple or suture line as well as covers the juncture of the tissues to reduce leakage prior to healing.

The complexity of surgical stapling is apparent in pancreatic surgical procedures which can be technically challenging and have a high chance of post-operative complications. The location of the pancreas behind major organs can make access to the resection site difficult, constraining the reach and articulation range of surgical instruments. Further, reconnection of the pancreatic remnant to the bowel is a critical step that can result in internal leakage and fistula. Pancreatic fistula is a major source of patient morbidity and mortality, resulting in complications such as inflammation and sepsis. These complications may require drainage, intensive therapy, and/or re-operation which can add significant cost and extend the length of hospital stay.

Another constraint of pancreatic surgery is the tissue quality of the pancreas. For example, the friability, thickness, and density of the tissue factor into how the tissue is to be handled. Further still, current surgical stapling apparatus and methods may apply excessive force to manipulate and fit the tissue between the jaws, which can result in tissue trauma and delayed leaks. The tissue may be crushed or put under excess tension which can result in bursting during or after the procedure.

Accordingly, a surgeon must examine various factors and mitigation strategies for potential complications. The surgeon must decide the appropriate staple cartridge to use, the appropriate clamping height for the tissue, and if a surgical support is necessary to reinforce the tissue.

SUMMARY

The present disclosure relates to a device and a method for handling and resecting tissue to reduce post-operative complications. The device includes an extendable buttress material that enables a more delicate grasping of tissue with greater surface area that just the surface area of the stapler's jaws. The method includes a three step jaw approximation technique which reduces tension at the staple line due to gradual tissue compression and extended tissue relaxation and decreases the likelihood of post-operative complications (e.g., leaks). The device and the method can be combined for delicate tissue manipulation, with gradual deployment of the buttress material during the jaw approximation and firing steps.

In one aspect, the present disclosure provides a loading unit for a surgical stapling apparatus including an anvil assembly, a staple cartridge assembly, and a surgical buttress assembly operably associated with the anvil or staple cartridge assembly. The anvil assembly has a tissue facing surface defining a central longitudinal slot and staple forming pockets therein. The staple cartridge assembly has a tissue facing surface defining a central longitudinal slot and staple pockets therein. The surgical buttress assembly includes a buttress material positioned on the tissue facing surface of the anvil or staple cartridge assembly and a buttress frame supporting the buttress material. The buttress frame is movable from an undeployed position in which the buttress frame retains the buttress material within the boundaries of the tissue facing surface of the anvil or staple cartridge assembly to a deployed position in which the buttress frame extends the buttress material laterally outwardly from the anvil or staple cartridge assembly.

The buttress material may include a pocket defined around a periphery thereof, and the buttress frame may extend through the pocket.

A proximal portion of the buttress frame may be longitudinally movable relative to a distal portion of the buttress frame. The distal portion of the buttress frame may be releasably coupled to the tissue facing surface of the anvil or staple cartridge assembly.

The surgical buttress assembly may further include a buttress drive rod coupled to a proximal portion of the buttress frame and extending proximally therefrom.

The buttress frame may include a pair of arms aligned with longitudinal edges of the tissue facing surface of the anvil or staple cartridge assembly. Distal movement of a proximal portion of the buttress frame may flex the arms outwardly beyond the longitudinal edges.

A distal portion of the buttress frame may include a pair of arched sections. The distal portion of the buttress frame may include a base disposed between the pair of arched sections. The base may overlie the central longitudinal slot of the anvil or staple cartridge assembly.

The loading unit may further include a drive assembly including a knife blade translatable through the central longitudinal slots of the anvil and staple cartridge assemblies. The knife blade may be configured to cut the base of the buttress support at the end of a firing stroke of the drive assembly.

Approximation of the anvil and staple cartridge assemblies relative to each other may move the surgical buttress assembly from an undeployed state in which the buttress frame is in the undeployed position to a deployed state in which the buttress frame is in the deployed position.

The loading unit may further include a second surgical buttress assembly associated with the other of the anvil and staple cartridge assembly.

In another aspect, the present disclosure provides a method of treating tissue including: positioning an anvil assembly and a staple cartridge assembly of a loading unit of a surgical stapling apparatus on first and second sides of a tissue; moving the anvil and staple cartridge assemblies to a tissue grasping position in which tissue facing surfaces of the anvil and staple cartridge assemblies are disposed at a first clamping distance relative to each other; moving the anvil and staple cartridge assemblies to a tissue clamping position in which the tissue facing surfaces of the anvil and staple cartridge assemblies are disposed at a second clamping distance relative to each other; and moving the anvil and staple cartridge assemblies to a tissue stapling position in which the tissue facing surfaces of the anvil and staple cartridge assemblies are disposed at a third clamping distance relative to each other.

The first clamping distance may be greater than the second clamping distance, and the second clamping distance may be greater than the third clamping distance.

The method may further include waiting a pre-determined period of time between moving the anvil and staple cartridges from the tissue clamping position to the tissue stapling position.

Moving the anvil and staple cartridge assemblies to the tissue grasping position may include actuating an actuator of a handle assembly of the surgical stapling apparatus to move the anvil and staple cartridge assemblies to the tissue grasping position.

The handle assembly may be powered and actuating the actuator may automatically moves the anvil and staple cartridge assemblies to the tissue clamping position and the tissue stapling position after set periods of time between each position.

A surgical buttress assembly may be associated with the anvil or staple cartridge assembly. The surgical buttress assembly may include a buttress material disposed over the tissue facing surface of the anvil or staple cartridge assembly. Positioning the anvil assembly and the staple cartridge assembly may include positioning the buttress material against the first or second side of the tissue, the buttress material disposed in an undeployed position having at a first extension distance relative to a longitudinal edge of the anvil or staple cartridge assembly.

Moving the anvil and staple cartridge assemblies to the tissue clamping position may include moving the buttress material to a semi-deployed position having a second extension distance relative to the longitudinal edge of the anvil or staple cartridge assembly.

Moving the anvil and staple cartridge assemblies to the tissue stapling position may include moving the buttress material to a fully deployed position having a third extension distance relative to the longitudinal edge of the anvil or staple cartridge assembly.

The first extension distance may be zero, the second extension distance may be greater than the first extension distance, and the third extension distance may be greater than the second extension distance.

Moving the anvil and staple cartridge assemblies to the tissue stapling position may include deploying a knife blade and staples to sever and staple the tissue.

The details of one or more aspects of the disclosure are set forth in the accompanying drawings and the description below. Other aspects, as well as features, objects, and advantages of the aspects described in this disclosure will be apparent from the description and drawings, and from the claims.

BRIEF DESCRIPTION OF DRAWINGS

FIG. 4 is top view of a surgical buttress assembly of the surgical stapling apparatus of FIG. 1;

FIG. 5 is a cross-sectional view of the surgical buttress assembly of FIG. 4, taken along section line 5-5 of FIG. 4;

FIG. 11 is an end view of the end effector of FIG. 10, shown in a tissue stapling position with the surgical buttress assembly in the fully deployed state of FIG. 8; and FIG. 12 is a side view of the tissue of FIGS. 9-11, after a firing stroke of the surgical stapling apparatus of FIG. 1.

DETAILED DESCRIPTION

Figure 1:
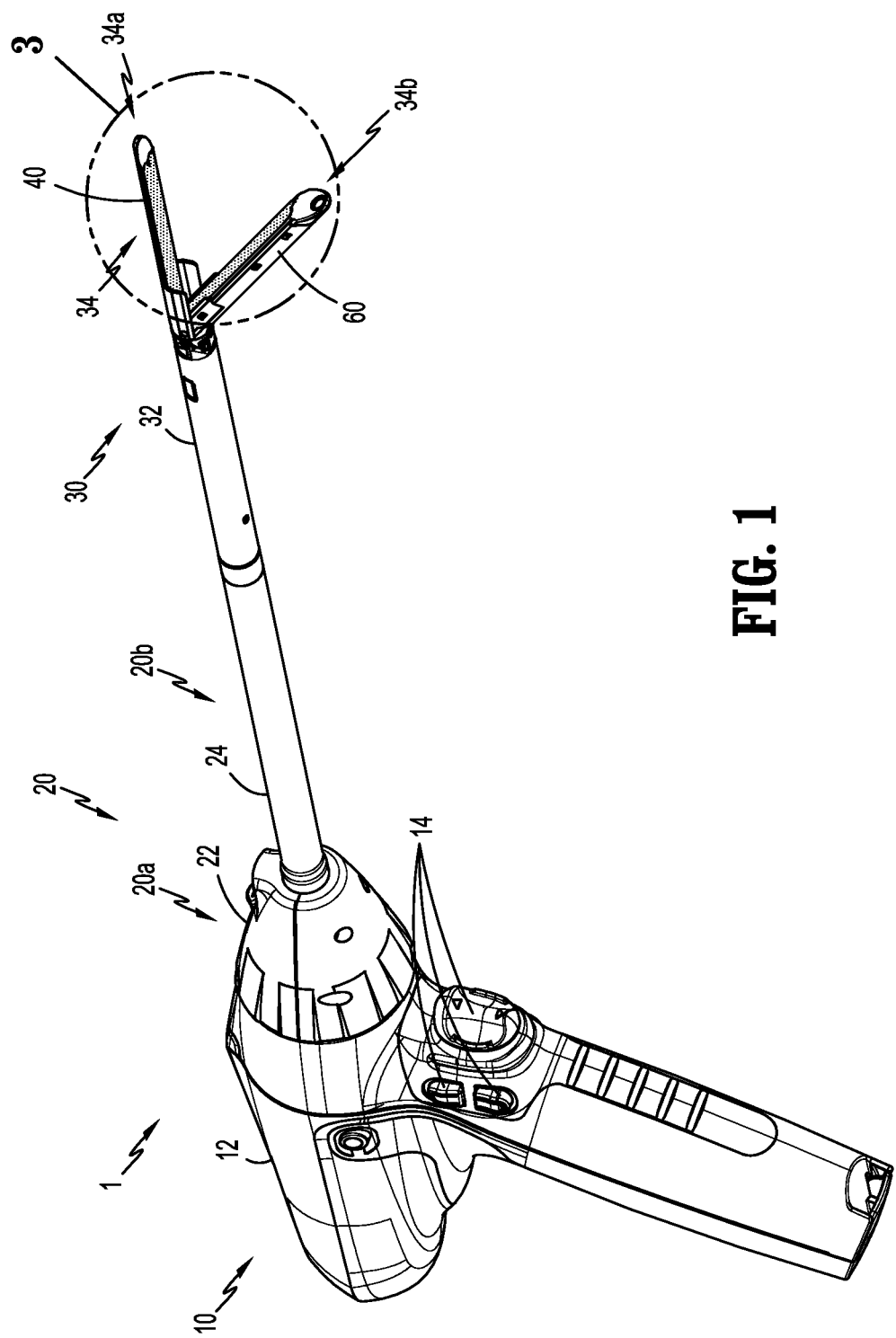
FIG. 1 is a perspective view of a surgical stapling apparatus in accordance with an aspect of the present disclosure.

Embodiments of the present disclosure will now be described in detail with reference to the drawing figures wherein like reference numerals identify similar or identical elements. Throughout this description, the term "proximal" refers to a portion of a structure, or component thereof, that is closer to a user, and the term "distal" refers to a portion of the structure, or component thereof, that is farther from the user. The terms "generally," "substantially," and "about" shall be understood as words of approximation that take into account relatively little to no variation in the modified terms (e.g., differing by less than 10%).

Although the surgical buttress assemblies and techniques of the present disclosure offers significant advantages during a pancreas resection procedure, it will be understood that the surgical buttress assemblies and techniques are applicable for use in a variety of surgical stapling procedures or may be modified to accommodate other anastomotic procedures, organs, and/or tissue types.

Referring now to FIG. 1, a surgical stapling apparatus or device 1 is shown in the form of a powered handheld electromechanical surgical instrument. The surgical device 1 includes a powered handle assembly 10, an adapter assembly 20, and a loading unit or end effector 30. The powered handle assembly 10 is configured for selective connection with the adapter assembly 20 and, in turn, the adapter assembly 20 is configured for selective connection with the end effector 30.

The surgical device 1 will only further be described to the extent necessary to disclose aspects of the present disclosure. For a detailed description of the structure and function of exemplary surgical devices, and components thereof, reference may be made to commonly owned U.S. Patent Publication Nos. 2015/0157320, 2015/0157321, 2016/0296234, 2016/0310134, and 2018/0360460, the entire contents of each of which are incorporated herein by reference.

With continued reference to FIG. 1, the powered handle assembly 10 includes a handle housing 12 housing a powerpack (not shown) configured to power and control various operations of the surgical device 1, and a plurality of actuators 14 (e.g., finger-actuated control buttons, knobs, toggles, slides, interfaces, and the like) for activating various functions of the surgical device 1. The adapter assembly 20 has a proximal portion 20a including a knob housing 22 configured for operable connection to the handle assembly 10 and a distal portion 20b including an outer tube or elongate tubular body 24 configured for operable connection to the end effector 30. The end effector 30 includes a proximal body portion 32 and a jaw assembly 34 attached to the proximal body portion 32. The jaw assembly 34 includes a first jaw 34a including an anvil assembly 40 and a second jaw 34b including a staple cartridge assembly 60.

Figure 2:
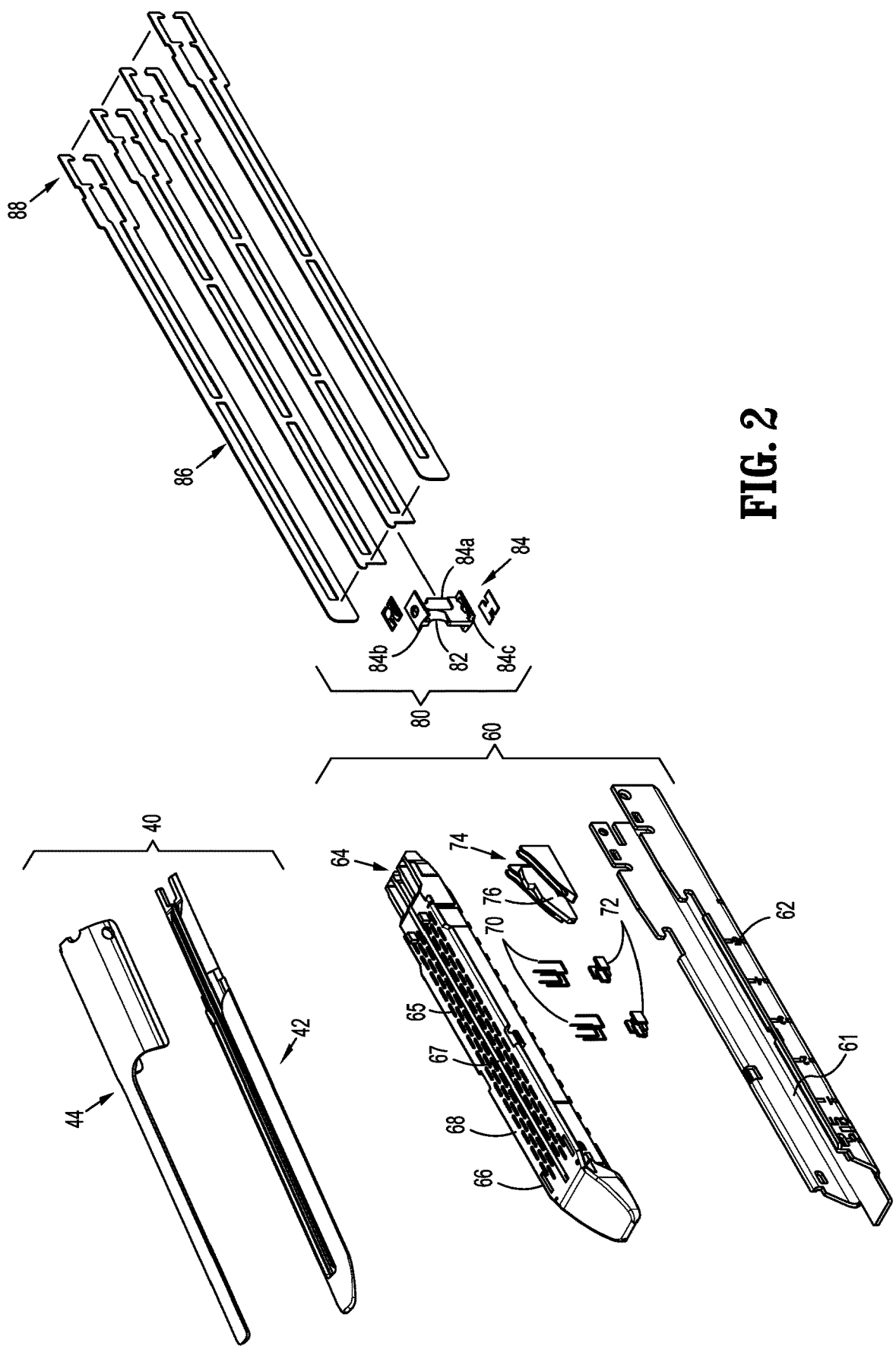
FIG. 2 is an exploded, perspective view of a jaw assembly and a drive assembly of an end effector of the surgical stapling apparatus of FIG. 1.

The end effector 30 may be a disposable loading unit ("DLU") that is releasably secured to the elongated tubular body 24 of the adapter assembly 20 and thus, replaceable with a new end effector 30 (e.g., a new DLU). The end effector 30 may be a single use loading unit ("SULU") that is used one time and then replaced to facilitate multiples uses of the surgical stapling apparatus 1 on a patient. For example, during a surgical procedure, the surgical stapling apparatus 1 can be used to staple and cut tissue, and the entire SULU is replaced after each staple and cut operation of the surgical stapling apparatus 1. The end effector 30 may be a multi-use loading unit ("MULU") that is re-useable a predetermined number of times. For example, during a surgical procedure, the surgical stapling apparatus 1 can be used to staple and cut tissue, and a reload assembly (e.g., a staple cartridge 64 as seen in FIG. 2) of the MULU is replaced after each staple and cut operation of the surgical stapling apparatus 1 a pre-determined number of times before the entire MULU needs to be replaced. Alternatively, the end effector 30 may be permanently affixed to the elongated tubular body 24.

As shown in FIG. 2, the anvil assembly 40 includes an anvil plate 42 and a cover plate 44 secured over the anvil plate 42. The anvil plate 42 has an inner or tissue facing surface 44 (FIG. 6) defining a central longitudinal or knife slot 43 and staple forming pockets or cavities 45 defined therein.

The staple cartridge assembly 60 of the end effector 30 includes a cartridge carrier 62 defining an elongated support channel 61 configured and dimensioned to selectively receive a staple cartridge 64 therein. The staple cartridge 64 may be removably and replaceably attached to the cartridge carrier 62 by, for example, a snap-fit connection, a detent, a latch, among other types of connectors within the purview of those skilled in the art. The staple cartridge 64 includes a cartridge body 66 having an inner or tissue facing surface 68 defining staple pockets or retention slots 65 formed therein for receiving a plurality of fasteners or staples 70 and staple pushers 72. An actuation sled 74 is translatable through the staple cartridge 64 to advance cam wedges 76 of the actuation sled 74 into sequential contact with the staple pushers 72. A central longitudinal or knife slot 67 is formed in and extends along a substantial length of the staple cartridge 64 to facilitate passage of a knife blade 82 of a drive assembly 80 therethrough.

The drive assembly 80 includes an elongated drive beam 86 having a connector 88 at a proximal end thereof that is configured to releasably engage a drive member or firing rod (not shown) of the adapter assembly 20, and an I-beam 84 at a distal end thereof. The I-beam 84 includes a vertical or central strut 84a interconnecting an upper or first beam 84b and a lower or second beam 84c. The knife 82 is defined in a distal face of the vertical strut 84a. The vertical strut 84a of the I-beam 84 is slidably disposed between the anvil and staple cartridge assemblies 40, 60, with the upper and lower rails 84b, 84c of the I-beam 84, respectively, supported in the anvil and staple cartridge assemblies 40, 60. Accordingly, during operation of the surgical stapling apparatus 1, the drive member imparts axial movement to the elongated drive beam 86 and thus, the I-beam 84. Distal advancement of the I-beam 84 causes the actuation sled 74 to translate through the staple cartridge 64 and to advance the cam wedges 76 into sequential contact with the staple pushers 72 which, in turn, cause the staple pushers 72 to translate vertically within the staple pockets 65 and urge the staples 70 from the staple pockets 65 towards the tissue facing surface 44 of the anvil plate 42 of the anvil assembly 40.

Figure 3:
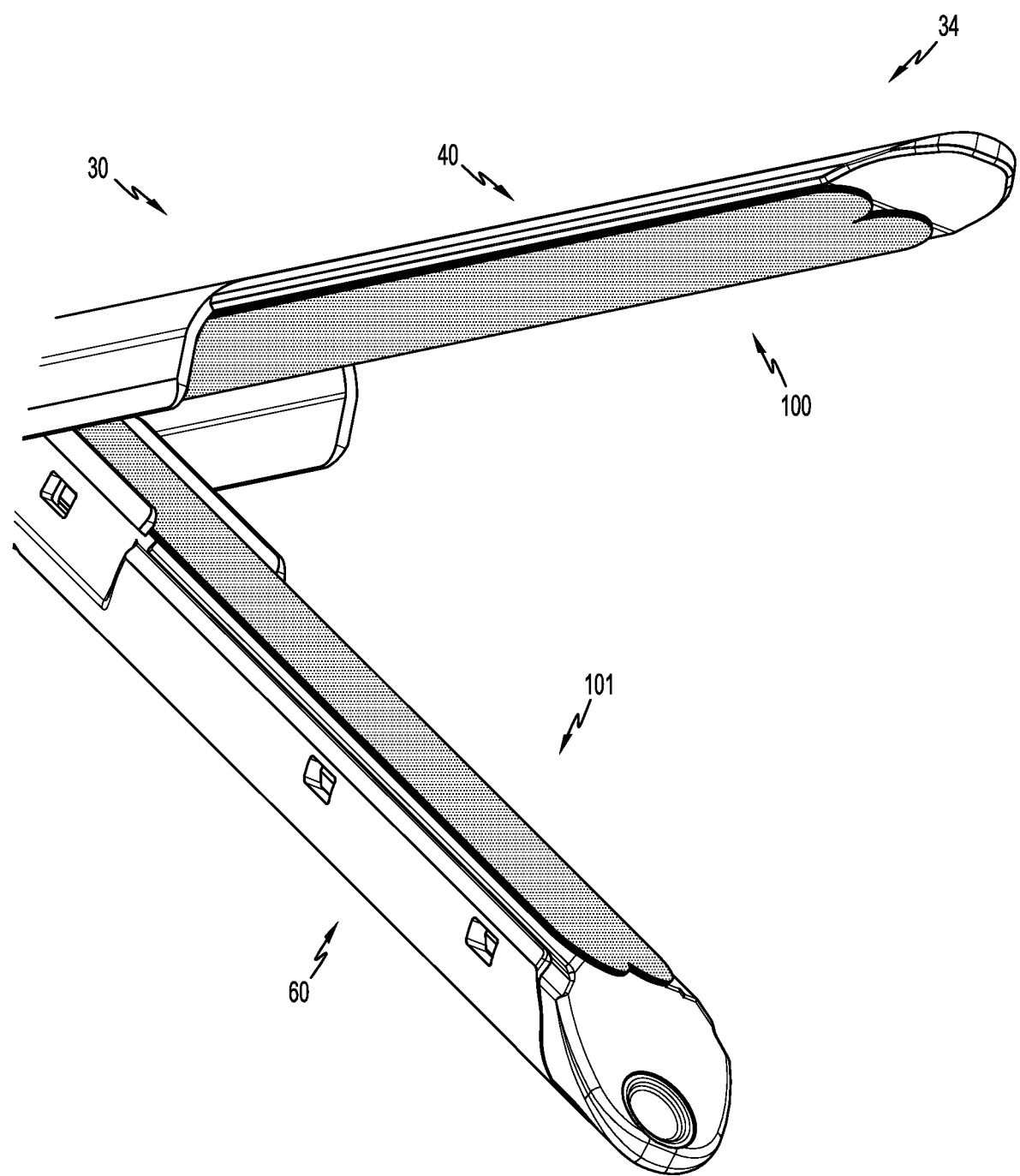
FIG. 3 is a close-up view of a jaw assembly of an end effector of the surgical stapling apparatus of FIG. 1.

As shown in FIG. 3, anvil and cartridge buttress assemblies 100, 101 (also referred to herein generally as surgical buttress assemblies) are shown releasably secured to the anvil and staple cartridge assemblies 40, 60, respectively, of the jaw assembly 34. In aspects, the surgical buttress assemblies 100, 101 are pre-loaded (e.g., by the manufacturer) onto the end effector 30. While the end effector 30 is shown including both surgical buttress assemblies 100, 101, it should be understood that only one of the surgical buttress assemblies 100, 101 may be utilized with the end effector 30 during a surgical stapling procedure. Further, while the surgical buttress assembly 100 associated with the anvil assembly 40 is discussed singularly hereinbelow, it should be understood that the surgical buttress assembly 101 associated with the staple cartridge assembly 60 is substantially the same or identical to the surgical buttress assembly 100.

Figure 6:
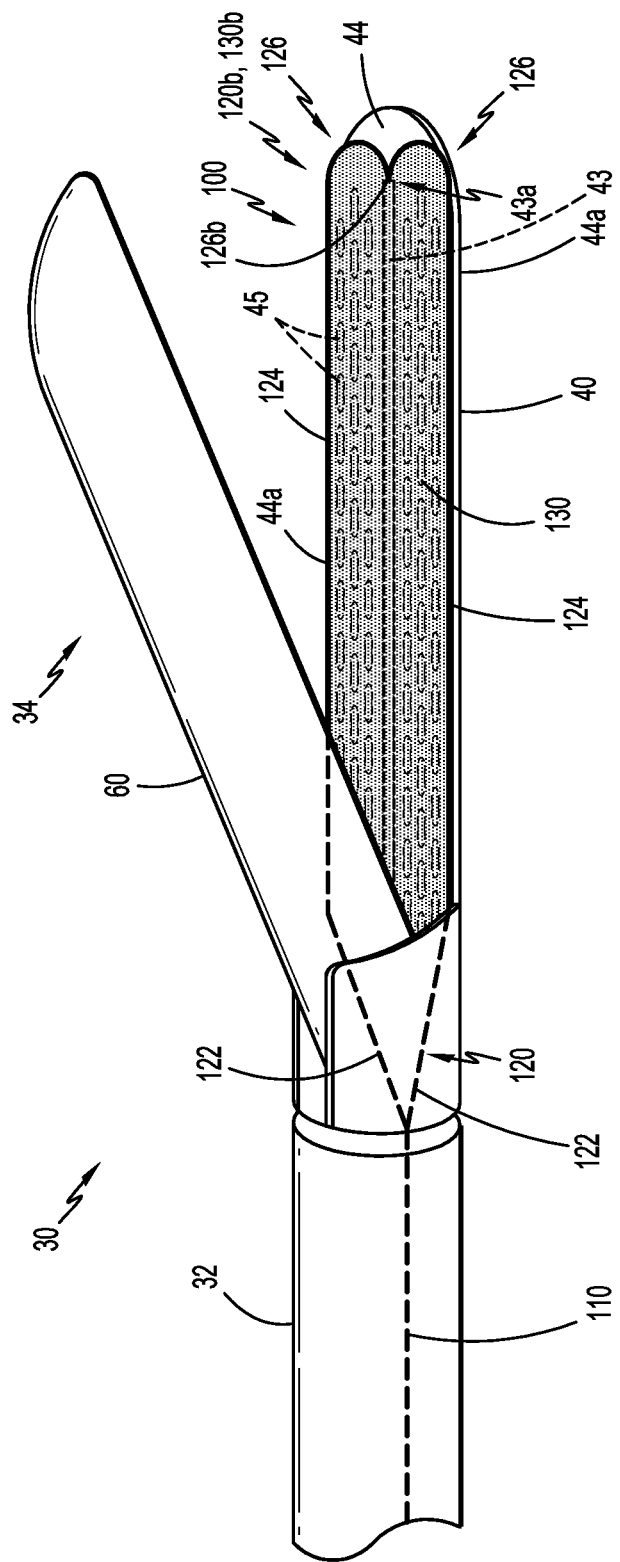
FIG. 6 is a side, perspective view of an end effector of the surgical stapling apparatus of FIG. 1, shown with a surgical buttress assembly in an undeployed state.

Turning now to FIGS. 4-6, the surgical buttress assembly 100 includes a buttress drive rod 110, a buttress frame 120, and a buttress material 130. The buttress drive rod 110 has an elongate body 112 configured for slidable longitudinal movement within the end effector 30 (FIG. 1) in response to actuation of the surgical device 1. The buttress drive rod 110 is slidable (e.g., via a mechanical or electromechanical connection for a slide, switch or button of the powered handle assembly 10) by reciprocal translational movement prior to, during, or following, approximation of the anvil and staple cartridge assemblies 40, 60. A distal end 110b of the buttress drive rod 110 is operably coupled to a proximal portion 120a of the buttress frame 120.

The buttress frame 120 extends distally from the buttress drive rod 110. The buttress frame 120 has a closed loop-like configuration defining an opening 121 therethrough. The buttress frame 120 includes a pair of legs 122 that bifurcate at the proximal portion 120a of the buttress frame 120. The pair of legs 122 are angled away from each other and extend distally and outwardly to a pair of arms 124 that are biased to extend substantially parallel to each other. The pair of arms 124 are sized and spaced to be in registration or alignment with longitudinal edges 44a of the tissue facing surface 44 of the anvil assembly 40 when the surgical buttress assembly 100 is positioned on the anvil assembly 40 and disposed in an undeployed state, as seen in FIG. 6.

A distal portion 120b of the buttress frame 120 includes a pair of arched sections 126 that each curve distally from the respective arm 124 towards an apex 126a and curve proximally from the apex 126a to a base 126b disposed between the arched sections 126 and shared by the arched sections 126. The distal portion 120b is configured such that the arched sections 126 extend distally beyond the staple forming pockets 45 defined in the tissue facing surface 44 of the anvil assembly 40 with the base 126b in registration or alignment with a distal end portion 43a of the central longitudinal slot 43 defined in the tissue facing surface 44 and releasably secured thereto. The buttress frame 120 supports the buttress material 130 such that the buttress material 130 extends across and along the opening 121 defined therein.

The buttress material 130 includes a buttress body 132 having a proximal end 132a, a distal end 132b, and longitudinal sides 132c. A pocket 131 is defined around a periphery of the buttress body 132 and is configured to receive the buttress frame 120 therein. The pocket 131 is open at the proximal end 132a of the buttress body 132 and extends continuously through the longitudinal sides 132c and the distal end 132b of the buttress body 132. Accordingly, the distal end 132b and the longitudinal sides 132c of the buttress body 132 conform to the size and shape of the buttress frame 120 described above. The pocket 131 may be formed using techniques within the purview of those skilled in the art such as, for example, folding, layering, molding, etc. of the buttress material 130.

The buttress material 130 is sized and shaped to cover the tissue facing surface 44 of the anvil assembly 40 (e.g., to cover the staple forming pockets 45 and the central longitudinal slot 43) and be expanded (e.g., stretched) beyond the longitudinal edges 44a of the tissue facing surface 44 upon actuation of the buttress drive rod 110 and movement of the buttress frame 120, as described in detail below.

The buttress material 130 may be fabricated from biocompatible materials which are bioabsorbable or non-absorbable, natural or synthetic materials. It should be understood that any combination of natural, synthetic, bioabsorbable, and/or non-bioabsorbable materials may be used to form the buttress material 130.

The buttress material 130 may be porous, non-porous, or combinations thereof. Suitable porous structures include, for example, fibrous structures (e.g., knitted structures, woven structures, and non-woven structures) and/or foams (e.g., open or closed cell foams). Suitable non-porous structures include, for example, films. The buttress material 130 described herein may be a single porous or non-porous layer, or include a plurality of layers including any combination of porous and non-porous layers. For example, the buttress material 130 may include multiple porous and non-porous layers that are stacked in an alternating manner. In another example, the buttress material 130 may be formed in a "sandwich-like" manner wherein the outer layers of the buttress material 130 are porous and the inner layer(s) are non-porous, or vice versa. The buttress materials 130 of the anvil and cartridge buttress assemblies 100, 101 may have the same or a different structure of layer(s).

Porous layer(s) may enhance the ability of the surgical buttress to absorb fluid, reduce bleeding, and/or seal a wound. Also, the porous layer(s) may allow for tissue ingrowth to fix the surgical buttress in place. Non-porous layer(s) may enhance the ability of the surgical buttress to resist tears and perforations during the manufacturing, shipping, handling, and/or stapling processes. Also, non-porous layer(s) may retard or prevent tissue ingrowth from surrounding tissues thereby acting as an adhesion barrier and preventing the formation of unwanted scar tissue.

The buttress drive rod 110 is substantially rigid so that the buttress drive rod 110 can be driven longitudinally within the end effector 30 without deformation. The buttress frame 120 is substantially flexible so that the arms 124 of the buttress frame 120 can be deformed in response to movement of the proximal portion 120a of the buttress frame 120 by the buttress drive rod 110 towards and away from the distal portion 120b of the buttress frame 120 which is releasably fixed to the anvil assembly 40. The buttress material 130 is pliable or provided with slack, folds, or crenellations, within the buttress frame 120 so that the buttress material 130 can expand in response to deformation of the buttress frame 120. Specifically, upon distal movement of the buttress drive rod 110 (relative to the buttress material 130, and specifically relative to the pair of arched sections 126 of buttress material 130), the arms 124 of the buttress frame 120 flex or bow laterally outwardly thereby expanding the buttress material 130 laterally outwardly beyond the anvil assembly 40.

The buttress drive rod 110 and the buttress frame 120 may be separate components connected together, or may be integrally formed from a single material (e.g., plastic or metal) with dimensions (e.g., diameters and/or lengths) of each of the components chosen so that the buttress drive rod 110 and the buttress frame 120 have the desired characteristics discussed above. The buttress material 130 may be formed from a mesh or other stretchable, elasticized, or yieldable structure within the purview of those skilled in the art.

With continued reference to FIG. 6, the surgical buttress assembly 100 is shown assembled onto the anvil assembly 40 in a first or undeployed state. In the undeployed state, the buttress drive rod 110 is disposed within the proximal portion 32 of the end effector 30 and the buttress material 130 overlies the tissue facing surface 44 of the anvil assembly 40. The legs 122 of the buttress frame 120 are disposed proximal of the staple forming pockets 45 defined in the tissue facing surface 44 of the anvil assembly 40, the arms 124 extend along the longitudinal edges 44a of the tissue facing surface 44 with the buttress material 130 extending therebetween, and the distal portions 120b, 130b of the buttress frame 120 and the buttress material 130 extend distally beyond the staple forming pockets 45. The base 126b of the distal portion 120b of the buttress frame 120 overlies the distal end 43a of the central longitudinal slot 43 and is secured thereover. The buttress frame 120 and/or the buttress material 130 may be secured to the anvil assembly 40 by any suitable attachment feature within the purview of those skilled in the art, such as, for example, mechanical attachment features (e.g., sutures, pins), chemical attachment features (e.g., adhesive), and/or attachment methods (e.g., welding). In aspects, the base 126b may extend into the central longitudinal slot 43 and be retained therein in a friction fit manner. Upon full actuation of the surgical device 1, the knife blade 82 is configured to cut the buttress frame 120 at the base 126b, severing the connection of the buttress material 130 from the anvil assembly 40 and cutting the buttress frame 120 in half.

Figure 7:
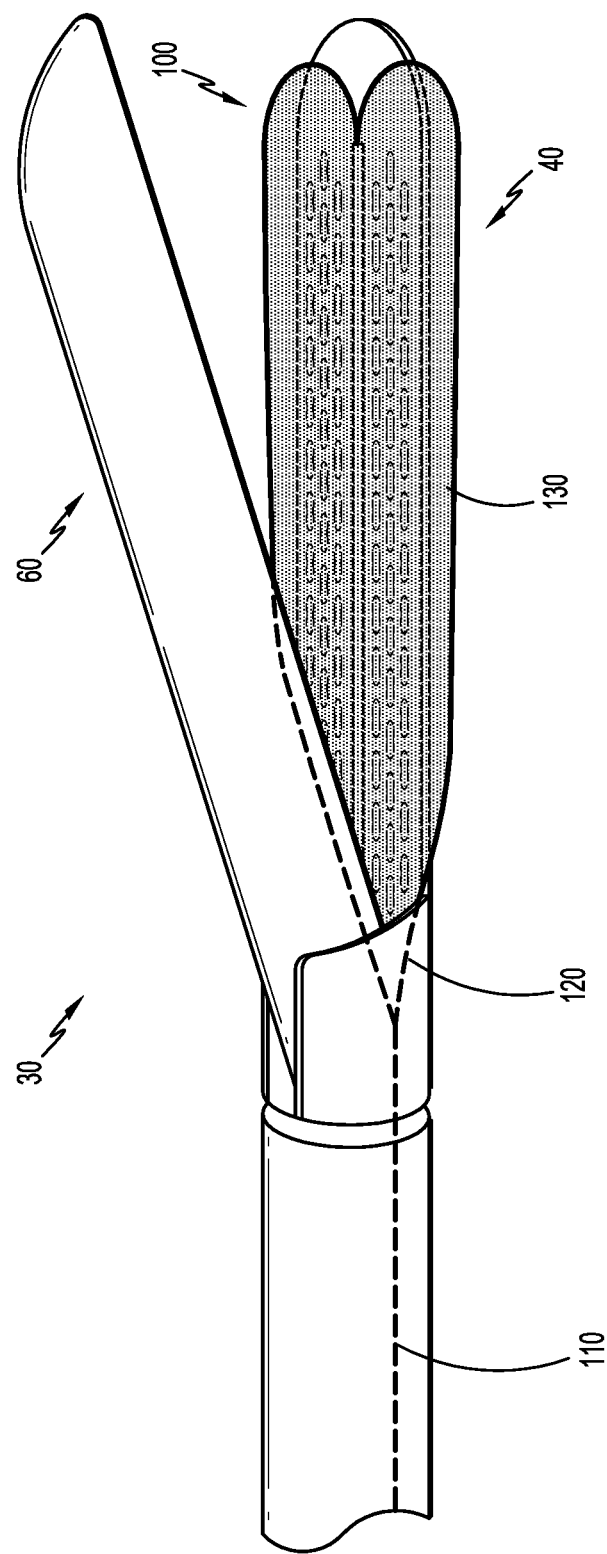
FIG. 7 is a side, perspective view of an end effector of the surgical stapling apparatus of FIG. 1, shown with a surgical buttress assembly in a semi-deployed state.
Figure 8:
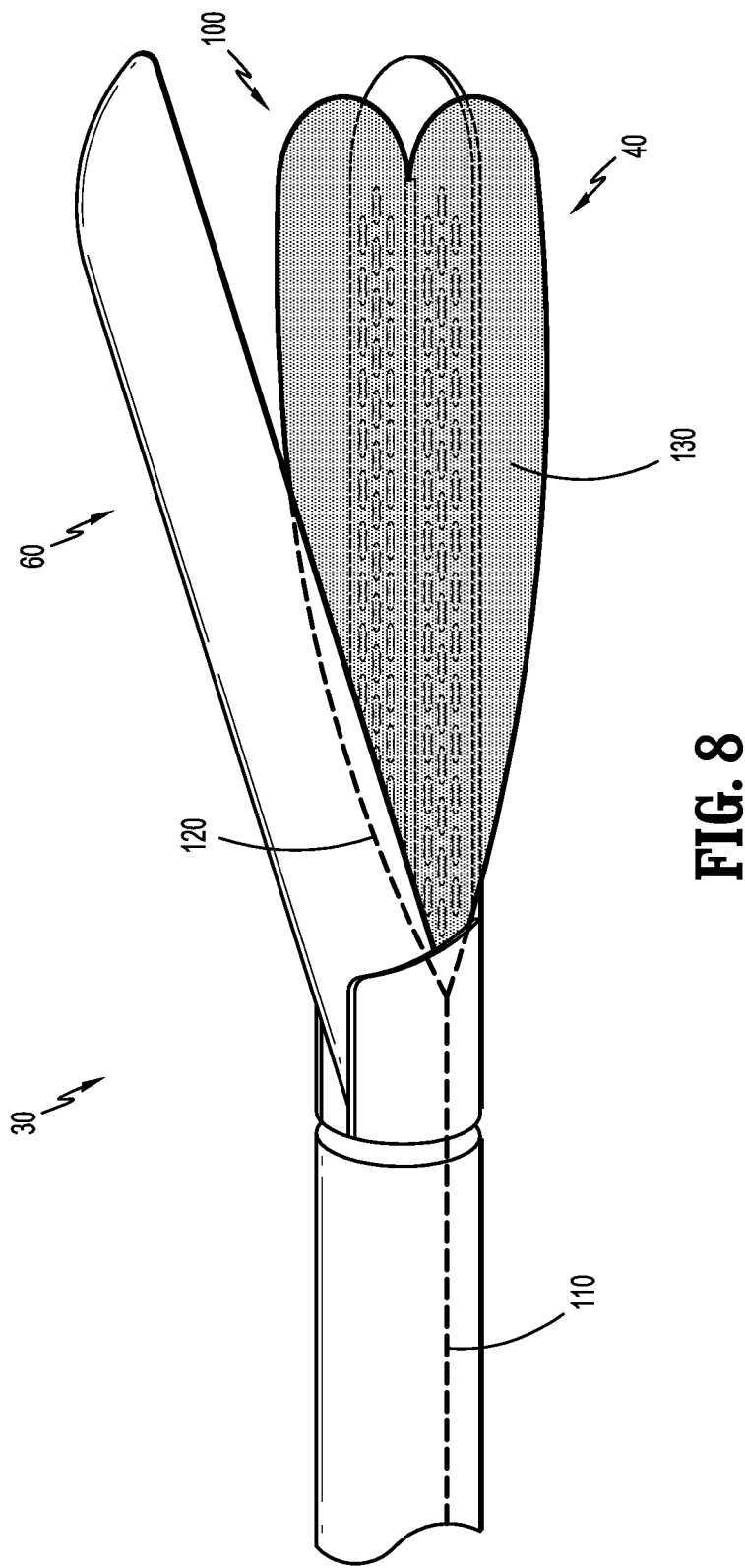
FIG. 8 is a side, perspective view of an end effector of the surgical stapling apparatus of FIG. 1, shown with a surgical buttress assembly in a fully deployed state.

In this undeployed state, the buttress drive rod 110 is in a proximal position, the buttress frame 120 is in an unexpanded position such that the buttress material 130 is also in an unexpanded position. The buttress drive rod 110 is movable in a distal direction (relative to the buttress material 130) during approximation of the anvil and staple cartridge assemblies 40, 60 which, in turn, drive the anvil buttress assembly 100 to a second or semi-deployed state, as shown in FIG. 7. In the semi-deployed state, the buttress drive rod 110 is in an intermediate position that is distal to the proximal position, and the buttress frame 120 and the buttress material 130 are in semi-expanded positions. The buttress drive rod 110 is further movable in a distal direction (relative to the buttress material 130) during approximation of the anvil and staple cartridge assemblies 40, 60 to drive the anvil buttress assembly 100 to a third or fully deployed state, as shown in FIG. 8. In the fully deployed state, the buttress drive rod 110 is in a distal position and the buttress frame 120 and the buttress material 130 are in fully expanded positions.

Figure 9:
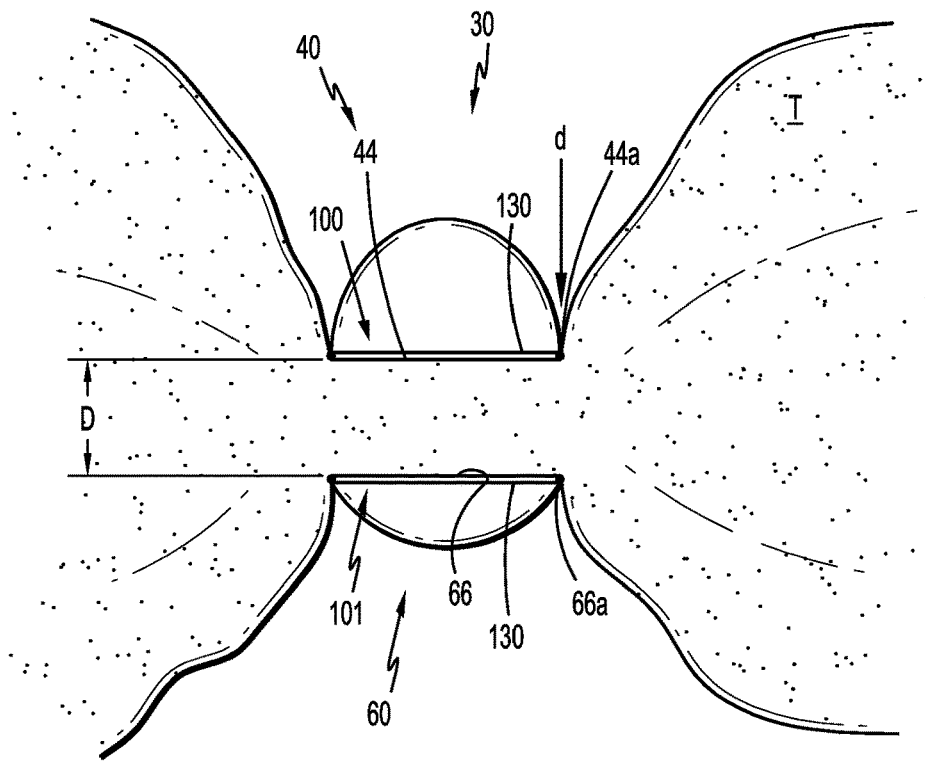
FIG. 9 is an end view of the end effector of FIG. 6 disposed around tissue, shown in a tissue grasping position in accordance with an aspect of the present disclosure.

Turning now to FIGS. 9-12, a method of use and operation of the surgical buttress assemblies 100, 101 is shown and described. The anvil and staple cartridge assemblies 40, 60, loaded with the surgical buttress assemblies 100, 101, are positioned adjacent to tissue "T" to be resected, such as pancreatic tissue. As seen in FIG. 9, the anvil and staple cartridge assemblies 40, 60 are moved to a first or tissue grasping position by, for example, actuating one of the actuators 14 (FIG. 1) of the handle assembly 10 of the surgical device 1. In the first position, the tissue "T" is grasped between the tissue facing surfaces 44, 66 of the anvil and staple cartridge assemblies 40, 60 containing the buttress materials 130 of the surgical buttress assemblies 100, 101 disposed thereon. The tissue "T" is grasped in this first approximation step so that a surgeon can manipulate the tissue "T" and the end effector 30 to get to the resection site. In this first position, the tissue facing surfaces 44, 66 are disposed at a first clamping distance "D" relative to each other and the buttress materials 130 are disposed at a first extension distance "d" relative to the longitudinal edges 44a, 66a of the anvil and staple cartridge assemblies 40, 60. In aspects, the first extension distance "d" is zero as the of the anvil and staple cartridge buttress assemblies 100, 101 are in the undeployed state seen in FIG. 6 and do not extend beyond the longitudinal edges 44a, 66a of the anvil and staple cartridge assemblies 40, 60.

Figure 10:
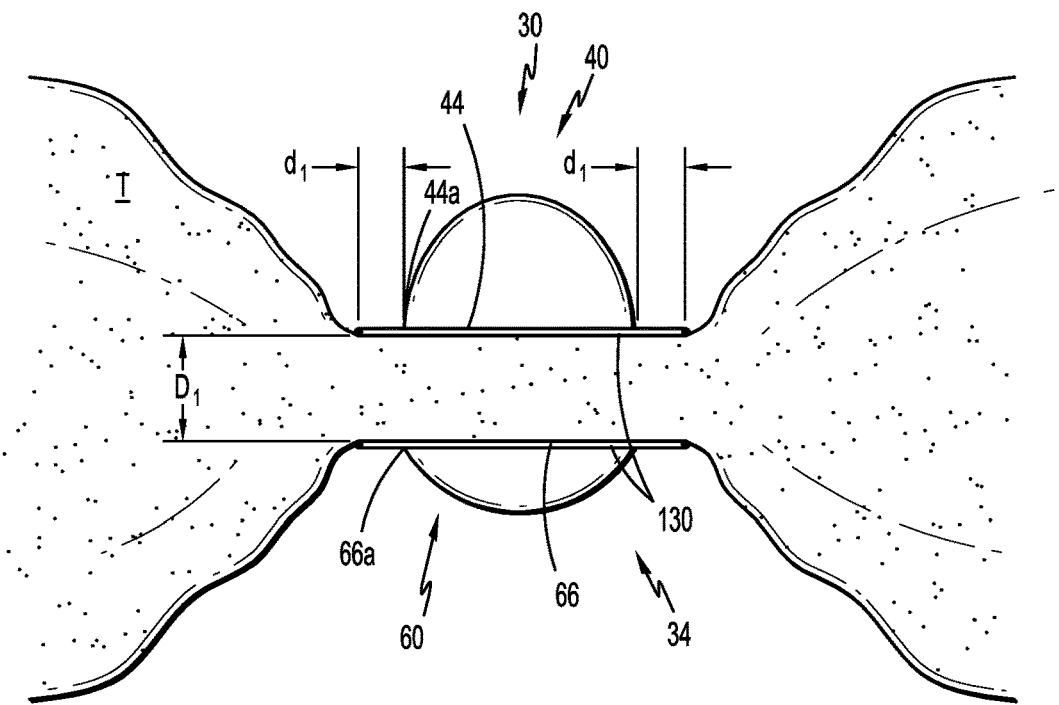
FIG. 10 is an end view of the end effector of FIG. 9, shown in a tissue clamping position with the surgical buttress assembly in the semi-deployed state of FIG. 7.

As seen in FIG. 10, with the end effector 30 positioned at the appropriate tissue location, the jaw assembly 34 is further approximated to a second or tissue clamping position in which the anvil and staple cartridge assemblies 40, 60 grasp the tissue "T" therebetween and compress the tissue "T." In the second position, the tissue facing surfaces 44, 66 are disposed a second clamping distance "D1" relative to each other, which is closer in distance than the first clamping distance "D," for a predetermined period of time to allow the tissue "T" to relax and for fluids to flow away from the clamped tissue. In aspects, the second clamping distance "D1" is about one half of the first clamping distance "D." The buttress materials 130 are disposed at a second extension distance "d1" relative to the longitudinal edges 44a, 66a of the anvil and staple cartridge assemblies 40, 60. The second extension distance "d1" extends laterally outwardly of the anvil assembly 40 and corresponds to the semi-deployed state seen in FIG. 7.

Approximation of the anvil and staple cartridge assemblies 40, 60 from the first to second positions causes a corresponding movement of the surgical buttress assemblies 100, 101 from the undeployed to the semi-deployed states as the buttress drive rod 110 is driven distally from the proximal position seen in FIG. 6 to the intermediate position seen in FIG. 7. Distal movement of the buttress drive rod 110 drives the proximal portion 120a of the buttress frame 120 distally. As the distal portion 120b of the buttress frame 120 is secured to the respective tissue facing surface 44, 66 of the anvil and staple cartridge assemblies 40, 60, the arms 124 of the buttress drive frame 120 are deflected outwardly during the distal movement of the proximal portion 120a relative to the distal portion 120b thereby expanding the buttress material 130 to the semi-expanded position.

As seen in FIG. 11, the jaw assembly 34 is still further approximated to a third or tissue stapling position in which the anvil and staple cartridge assemblies 40, 60 are positioned for firing of staples through the tissue "T." In the third position, the tissue facing surfaces 44, 66 are disposed at a third clamping distance "D2" which is closer in distance than the second clamping distance "D1" and equivalent to the stapling gap necessary to form the staples. The buttress materials 130 are disposed at a third extension distance "d2" which corresponds to the fully deployed state seen in FIG. 8 such that the buttress material 130 extends laterally outwardly of the anvil assembly 40.

The buttress materials 130 are fully deployed simultaneously with the firing of staples. Approximation of the anvil and staple cartridge assemblies 40, 60 from the second to third positions causes a corresponding movement of the surgical buttress assemblies 100, 101 from the semi-deployed to the fully deployed states as the buttress drive rod 110 is driven distally from the intermediate position seen in FIG. 7 to the distal position seen in FIG. 8. Distal movement of the buttress drive rod 110 drives the proximal portion 120a of the buttress frame 120 distally relative to the distal portion 120b such that the arms 124 of the buttress drive frame 120 are deflected outwardly thereby expanding the buttress material 130 to the fully expanded position.

During the firing stroke, the I-beam 84 advances through the anvil and staple cartridge assemblies 40, 60 to deploy the staples 70 (FIG. 12) and cut the tissue "T." When the I-beam 84 reaches the distal ends 43a, 67a of the central longitudinal slots 43, 67 of the anvil and staple cartridge assemblies 40, 60, the knife blade 82 cuts the buttress frames 120. After firing, as the buttress drive rod 110 is retracting proximally into the end effector 30, the buttress frames 120 are also retracted proximally from the pockets 131 of the respective buttress materials 130 thereby releasing the buttress materials 130 from the anvil and staple cartridge assemblies 40, 60.

As shown in FIG. 12, the tissue "T," now divided, has sealed stapled lines that are not under tension from the adjacent tissue. The staples 70 and the buttress materials 130 cover the periphery of the resection site, minimizing the likelihood of leaks that occur from excessive tension. The tissue is gradually relaxed during the jaw approximation process, enabling the flow of fluids away from the tissue grasped between the end effector, and deployment of the buttress materials beyond the staple line reduces tension experienced by the tissue.

The method described above may be a stapling algorithm (e.g., a pancreatic stapling algorithm) for a surgical stapling apparatus (e.g., a 3-step algorithm) programmed into the surgical device, with or without deployment of the surgical buttress assemblies 100, 101. Alternatively, the stapling algorithm can be user-directed with user timed approximation steps. It should be understood that such an algorithm or method may be tailored for specific procedures, organs, and/or tissue types to reduce post-operative complications and risks.

It should be understood that the surgical buttress assemblies and techniques described herein may be configured for use with other surgical apparatus, such as: manual surgical stapling devices as described, for example, in U.S. Pat. Nos. 8,256,656, 7,819,896, and 7,128,253; open staplers as described, for example, in U.S. Pat. No. 7,334,717; endoscopic staplers having radial or curved reloads as described, for example, in U.S. Pat. No. 8,360,298; transverse anastomosis staplers as described, for example, in U.S. Pat. No. 5,964,394; end-to-end anastomosis staplers having circular staple cartridge and anvil assemblies as described, for example, in U.S. Pat. Nos. 4,473,077, 5,119,983, and 5,915,616; as well as robotic surgical systems as described, for example, in U.S. Pat. No. 8,828,023, the entire content of each of which is incorporated herein by reference.

While aspects of the disclosure have been shown in the drawings, it is not intended that the disclosure be limited thereto, as it is intended that the disclosure be as broad in scope as the art will allow and that the specification be read likewise. It is to be understood, therefore, that the disclosure is not limited to the precise aspects described, and that various other changes and modifications may be affected by one skilled in the art without departing from the scope or spirit of the disclosure. Therefore, the above description should not be construed as limiting, but merely as exemplifications of aspects of the disclosure. Thus, the scope of the disclosure should be determined by the appended claims and their legal equivalents, rather than by the examples given.

What is claimed is:

1. A loading unit for a surgical stapling apparatus comprising:
   an anvil assembly having a tissue facing surface defining a central longitudinal slot and staple forming pockets therein;
   a staple cartridge assembly having a tissue facing surface defining a central longitudinal slot and staple pockets therein; and
   a surgical buttress assembly associated with the anvil assembly or the staple cartridge assembly, the surgical buttress assembly including:
      a buttress material positioned on the tissue facing surface of the anvil assembly or the staple cartridge assembly; and
      a buttress frame supporting the buttress material, the buttress frame movable from an undeployed position in which the buttress frame retains the buttress material within the boundaries of the tissue facing surface of the anvil assembly or the staple cartridge assembly to a deployed position in which the buttress frame extends the buttress material laterally outwardly from the anvil assembly or the staple cartridge assembly, wherein approximation of the anvil assembly and the staple cartridge assembly relative to each other moves the surgical buttress assembly from an undeployed state in which the buttress frame is in the undeployed position to a deployed state in which the buttress frame is in the deployed position.

2. The loading unit according to claim 1, wherein the buttress material includes a pocket defined around a periphery thereof, and the buttress frame extends through the pocket.

3. The loading unit according to claim 1, wherein a proximal portion of the buttress frame is longitudinally movable relative to a distal portion of the buttress frame, the distal portion releasably coupled to the tissue facing surface of the anvil assembly or the staple cartridge assembly.

4. The loading unit according to claim 1, wherein the surgical buttress assembly further includes a buttress drive rod coupled to a proximal portion of the buttress frame and extending proximally therefrom.

5. The loading unit according to claim 1, wherein the buttress frame includes a pair of arms aligned with longitudinal edges of the tissue facing surface of the anvil assembly or the staple cartridge assembly, and wherein distal movement of a proximal portion of the buttress frame flexes the arms outwardly beyond the longitudinal edges.

6. The loading unit according to claim 1, wherein a distal portion of the buttress frame includes a pair of arched sections.

7. The loading unit according to claim 6, wherein the distal portion of the buttress frame includes a base disposed between the pair of arched sections, the base overlying the central longitudinal slot of the anvil assembly or the staple cartridge assembly.

8. The loading unit according to claim 7, further including a drive assembly including a knife blade translatable through the central longitudinal slots of the anvil assembly and the staple cartridge assembly, the knife blade configured to cut the base of the buttress frame at the end of a firing stroke of the drive assembly.

9. The loading unit according to claim 1, further including a second surgical buttress assembly associated with the other of the anvil assembly or the staple cartridge assembly.

10. The loading unit according to claim 1, wherein the deployed position is one of a plurality of deployed positions.

11. A method of treating tissue, comprising:
   positioning an anvil assembly and a staple cartridge assembly of a loading unit of a surgical stapling apparatus on first and second sides of a tissue, the anvil assembly having a tissue facing surface defining a central longitudinal slot and staple forming pockets therein, the staple cartridge assembly having a tissue facing surface defining a central longitudinal slot and staple pockets therein, the anvil assembly or the staple cartridge assembly including a surgical buttress assembly associated therewith, the surgical buttress assembly including:
      a buttress material positioned on the tissue facing surface of the anvil assembly or the staple cartridge assembly; and
      a buttress frame supporting the buttress material, the buttress frame movable from an undeployed position in which the buttress frame retains the buttress material within the boundaries of the tissue facing surface of the anvil assembly or the staple cartridge assembly to a deployed position in which the buttress frame extends the buttress material laterally outwardly from the anvil assembly or the staple cartridge assembly; and
   approximating the anvil assembly and the staple cartridge assembly relative to each other to move the surgical buttress assembly from an undeployed state in which the buttress frame is in the undeployed position to a deployed state in which the buttress frame is in the deployed position.

12. The method according to claim 11, wherein approximating the anvil assembly and the staple cartridge assembly relative to each other includes:
   moving the anvil assembly and the staple cartridge assembly to a tissue grasping position in which tissue facing surfaces of the anvil assembly and the staple cartridge assembly are disposed at a first clamping distance relative to each other;
   moving the anvil assembly and the staple cartridge assembly to a tissue clamping position in which the tissue facing surfaces of the anvil assembly and the staple cartridge assembly are disposed at a second clamping distance relative to each other; and moving the anvil assembly and the staple cartridge assembly to a tissue stapling position in which the tissue facing surfaces of the anvil assembly and the staple cartridge assembly are disposed at a third clamping distance relative to each other.

13. The method according to claim 12, wherein the first clamping distance is greater than the second clamping distance, and the second clamping distance is greater than the third clamping distance.

14. The method according to claim 12, further including waiting a pre-determined period of time between moving the anvil assembly and the staple cartridge assembly from the tissue clamping position to the tissue stapling position.

15. The method according to claim 12, wherein moving the anvil assembly and the staple cartridge assembly to the tissue grasping position includes actuating an actuator of a handle assembly of the surgical stapling apparatus to move the anvil assembly and the staple cartridge assembly to the tissue grasping position.

16. The method according to claim 15, wherein the handle assembly is powered and actuating the actuator automatically moves the anvil assembly and the staple cartridge assembly to the tissue clamping position and the tissue stapling position after set periods of time between each position.

17. The method according to claim 12, wherein the deployed position of the buttress frame is one of a plurality of deployed positions, and wherein moving the anvil assembly and the staple cartridge assembly to the tissue clamping position includes moving the buttress material to a semi-deployed position of the plurality of deployed positions.

18. The method according to claim 17, wherein moving the anvil assembly and the staple cartridge assembly to the tissue stapling position includes moving the buttress material to a fully deployed position of the plurality of deployed positions.

19. The method according to claim 12, wherein moving the anvil assembly and the staple cartridge assembly to the tissue stapling position includes deploying a knife blade and staples to sever and staple the tissue.

20. A loading unit for a surgical stapling apparatus comprising:
   an anvil assembly having a tissue facing surface defining a central longitudinal slot and staple forming pockets therein;
   a staple cartridge assembly having a tissue facing surface defining a central longitudinal slot and staple pockets therein; and
   a surgical buttress assembly associated with the anvil assembly or the staple cartridge assembly, the surgical buttress assembly including:
      a buttress material positioned on the tissue facing surface of the anvil assembly or the staple cartridge assembly;
      a buttress frame supporting the buttress material, the buttress frame movable from an undeployed position in which the buttress frame retains the buttress material within the boundaries of the tissue facing surface of the anvil assembly or the staple cartridge assembly to a deployed position in which the buttress frame extends the buttress material laterally outwardly from the anvil assembly or the staple cartridge assembly; and
      a buttress drive rod coupled to a proximal portion of the buttress frame and extending proximally therefrom.

* * * * *